US008278358B2

(12) United States Patent
Eidenberger

(10) Patent No.: US 8,278,358 B2
(45) Date of Patent: Oct. 2, 2012

(54) LIPOIC ACID DERIVATIVES

(75) Inventor: Thomas Eidenberger, Steyr (AT)

(73) Assignee: Omnica GmbH, Hamburg (DE)

( * ) Notice: Subject to any disclaimer, the term of this patent is extended or adjusted under 35 U.S.C. 154(b) by 0 days.

(21) Appl. No.: 11/772,278

(22) Filed: Jul. 2, 2007

(65) Prior Publication Data

US 2008/0058406 A1 Mar. 6, 2008

Related U.S. Application Data

(60) Provisional application No. 60/947,018, filed on Jun. 29, 2007, provisional application No. 60/893,485, filed on Mar. 7, 2007.

(30) Foreign Application Priority Data

Jul. 7, 2006 (AT) ................................ A 1156/2006

(51) Int. Cl.
*A61K 31/13* (2006.01)
*A61K 31/385* (2006.01)
*C11D 1/28* (2006.01)

(52) U.S. Cl. .......... 514/665; 554/85; 514/440; 514/562; 514/785; 514/768; 514/788

(58) Field of Classification Search .................. 560/147; 514/440, 785; 554/85
See application file for complete search history.

(56) References Cited

U.S. PATENT DOCUMENTS

| 2,766,257 A | * | 10/1956 | Holly et al. ..................... 549/11 |
| 2,772,300 A | * | 11/1956 | Wagner ............................ 558/5 |
| 4,921,475 A | | 5/1990 | Sibalis | |
| 5,008,110 A | | 4/1991 | Benecke et al. | |
| 5,087,240 A | | 2/1992 | Sibalis | |
| 5,088,977 A | | 2/1992 | Sibalis | |
| 5,163,899 A | | 11/1992 | Sibalis | |
| 5,164,189 A | | 11/1992 | Farhadieh et al. | |
| 5,254,346 A | | 10/1993 | Tucker | |
| 5,290,561 A | | 3/1994 | Farhadieh et al. | |
| 5,336,168 A | | 8/1994 | Sibalis | |
| 5,352,213 A | | 10/1994 | Woodard | |
| 5,407,713 A | | 4/1995 | Wifong et al. | |
| 5,990,152 A | | 11/1999 | Hettche et al. | |
| 6,348,490 B1 | | 2/2002 | Hettche et al. | |
| 6,582,721 B1 | | 6/2003 | Lang | |
| 2002/0151578 A1 | * | 10/2002 | Breitenbach et al. ......... 514/440 |
| 2003/0148991 A1 | * | 8/2003 | Hahnlein et al. ................ 514/47 |

FOREIGN PATENT DOCUMENTS

JP 43-5820 * 4/1968

OTHER PUBLICATIONS

Berge, S.M. et al., Pharmaceutical Salts, 1977, Journal of Pharmaceutical Sciences, vol. 66, No. 1, pp. 1-19.*
Brown, P.R., The Investigatin of Some Reactins of Alpha-lipoic acid, 1969, Brown University, Ph.D. Thesis (168 pages).* JP 68005820 B, Fujisawa Pharm Co Ltd. 1964. English abstract of JP 43-5820, 2 pages.*
A. Smith et al., "Lipoic Acid as a Potential Therapy for Chronic Diseases Associated with Oxidative Stress," Current Medicinal Chemistry, May 2004, pp. 1135-1146.
P. Brown et al., "Effect of Solvent on the Photolysis of -Lipoic Acid," J. Organic Chemistry, Oct. 1999, pp. 3131-3135.
PCT/IB2007/004407 International Search Report.

* cited by examiner

*Primary Examiner* — Yate K Cutliff
(74) *Attorney, Agent, or Firm* — Scott D. Rothenberger; Fulbright & Jaworski L.L.P.

(57) ABSTRACT

The invention describes alpha lipoic acid complexes, that can be oligomeric, polymeric, monomeric and mixtures thereof. The complexes can be salts, chelates, etc. of the oligomers, polymers, or monomeric alpha lipoic acid.

31 Claims, 19 Drawing Sheets

LIPOIC ACID DERIVATIVES

CROSS REFERENCE TO RELATED APPLICATIONS

This application claims the benefit of priority to U.S. Provisional Application No. 60/947,018, filed on Jun. 29, 2007, U.S. Provisional Application No. 60/893,485, filed on Mar. 7, 2007, and Austrian Patent Application No. A1156/2006 filed on Jul. 7, 2006, the contents of which are incorporated in by reference.

FIELD OF THE INVENTION

The invention relates generally to oligomers of lipoic acid as well as oligomeric complexes of lipoic acid (thioctic acid) and, in particular, amino acid salts of oligomers of lipoic acid.

BACKGROUND OF THE INVENTION

Alpha-lipoic acid was first isolated as an acetate replacing factor. It is slightly soluble in water and soluble in certain organic solvents. Alpha-lipoic acid was initially identified as a vitamin after its isolation, but it was later found to be synthesized by mammals, including humans, as well as by plants. The complete enzyme pathway that is responsible for the de novo synthesis has not yet been definitively elucidated. Several studies have indicated that octanoate serves as the immediate precursor for the 8-carbon fatty acid chain, and cysteine appears to be the source of sulfur. As an amide (lipoamide), it functions as a cofactor in the multienzyme complexes that catalyze the oxidative decarboxylation of alpha-keto acids such as pyruvate, alpha-keto glutarate, and branched chain alpha-keto acids.

Alpha-lipoic acid is one of the strongest naturally occurring antioxidants. Alpha-lipoic acid (LA) is also known as thioctic acid, 1,2-dithiolane-3-pentanoic acid, 1,2-dithiolane-3-valeric acid and 6,8-thioctic acid. Alpha-lipoic acid has a chiral carbon atom and occurs in two enantiomeric forms (R— and S—). The form of alpha-lipoic acid sold in stores is a synthetic mixture of the natural isomer (R—) and the unnatural isomer (S—). The natural form of R-LA is not as stable as the synthetic mixture. One manufacturer, Asta Medica, sells R-LA for diabetes and has made a stable form of R-LA by crystallizing it with Tris buffer, a commonly used synthetic, but unnatural, buffer.

Various enantiomeric forms of alpha-LA, and combinations and derivatives thereof (including its reduced form), have been used to treat numerous conditions. For example, LA's have been used in the treatment of circulatory disorders. LAs and vitamins have been found useful for producing analgesic, anti-inflammatory, antinecrotic, anti-diabetic and other therapeutic effects. Certain alkylated derivatives of LA have been used in treatment of retroviral diseases.

Alpha-lipoic acid, and its reduced form, dihydrolipoic acid (DHLA) have antioxidant properties. Lipoate (a term for carboxylic acid esters and salts), or its reduced form, DHLA, reacts with reactive oxygen species such as superoxide radicals, hydroxyl radicals, hypochlorous acid, peroxyl radicals, and singlet oxygen. It also protects membranes by interacting with vitamin C and glutathione, which may in turn recycle vitamin E. In addition to its antioxidant activities, DHLA may exert prooxidant actions to reduction of iron. Alpha-lipoic acid administration has been shown to be beneficial in a number of oxidative stress models such as ischemia-reperfusion injury (IRI), diabetes (both alpha-lipoic acid and DHLA exhibit hydrophobic binding to proteins such as albumin, which can prevent glycation reactions), cataract formation, HIV activation, neurodegeneration, and radiation injury. Furthermore, lipoate can function as a redox regulator of proteins such as myoglobin, prolactin, thioredoxin, and NF-kappa-B transcription factor.

Lipoate may also have other activities. For example, DHLA has been found in vitro to be an anti-inflammatory agent which at the same time interferes with nitric oxide release from inflammatory macrophages and protects target cells from oxygen radical attack.

Lipoic acid is also a coenzyme for several enzymes. Lipoic acid is a coenzyme for both alpha-keto acid dehydrogenase complex enzymes (i.e. pyruvate dehydrogenase complex and alpha-keto glutarate dehydrogenase complex), branched chain alpha-keto acid dehydrogenase complex, and the glycine cleavage system. In the enzyme system, the body forms a multi-enzyme complex involving lipoic acid, that breaks down molecules of pyruvate produced in earlier metabolism, to form slightly smaller, high energy molecules, called acetyl-coenzyme A. This results in molecules that can enter into a series of reactions called the citric acid cycle, or Krebs cycle, which finishes the conversion of food into energy. Essentially, lipoic acid stimulates basal glucose transport and has a positive effect on insulin stimulated glucose uptake.

Under physiological conditions, LA exists as lipoamide in at least five proteins where it is covalently linked to a lysyl residue. Four of these proteins are alpha-ketoacid dehydrogenase complexes, the pyruvate dehydrogenase complex, the branched chain keto-acid dehydrogenase complex and the alpha-ketoglutarate dehydrogenase complex. Three lipoamide-containing proteins are present in the E2 enzyme dihydrolipoyl acyltransferase, which is different in each of the complexes and specific for the substrate of the complex. One lipoyl residue is found in protein X, which is the same in each complex. The fifth lipoamide residue is present in the glycine cleavage system.

Recently LA has been detected in the form of lipoyllysine in various natural sources. In the plant material studied, lipoyllysine content was highest in spinach. When expressed as weight per dry weight of lyophilized vegetables, the abundance of naturally existing lipoate in spinach was over three- and five-fold higher than that in broccoli and tomatoes, respectively. Lower concentrations of lipoyllysine were also detected in garden pea, Brussels sprouts and rice bran.

In animal tissues, the abundance of lipoyllysine in bovine acetone powders can be represented in the following order of 1) kidney, 2) heart, 3) liver, 4) spleen, 5) brain, 6) pancreas and 7) lung.

LA suffers from certain disadvantages, however. In particular, the natural form R-LA is unstable above 40° C., so it can degrade under some warehousing conditions. Also LA is hygroscopic. What is needed is stabilization of this natural form of LA with a natural salt.

Therefore, a need exists for compositions and/or methods to prepare alpha lipoic acid compositions in a manner that overcomes one or more of the identified current drawbacks of available materials.

BRIEF SUMMARY OF THE INVENTION

The present invention surprisingly provides complexes of alpha lipoic acid that are oligomeric.

The present invention also surprisingly provides oligomeric alpha lipoic acid as the "free acid".

Both the oligomeric complexes of alpha lipoic acid as well as the oligomeric "free acid" can be used to stabilize nutritional materials, such as carotenoids, that are otherwise considered to be not stabile to heat, oxidation, light, or other physical stresses that cause the material to degrade. The oligomeric complexes of alpha lipoic acid and the oligomeric free acid can be used in combination to help provide a stabilizing effect to the nutritional substance.

The exact nature of the alpha lipoic acid complexes (hereinafter "ALAC") of the invention have not been definitively determined, and not to be limited by theory, is believed that they are condensation products between two or more lipoic acids via sulfide bonds, thereby forming disulfides amongst two or more individual alpha lipoic acid units. The ALAC can be associated with at least one counterion, such as a metal salt, an amine or an amino acid, as well as others described infra.

Again, not to be limited by theory, it is possible that the ALAC's of the invention further include complexes of alpha lipoic acid that are "polymeric". That is, the condensation of greater than 50 alpha lipoic acid units result from a material that is bonded via multiple disulfide linkages amongst 50 or more individual alpha lipoic acid subunits.

In one aspect, the amount of polymeric ALAC is less than 10% (by weight), more particularly, less than 1%, even more particularly less than 0.5% and in a particular embodiment, less than 0.1% by weight.

The exact nature of the oligomeric alpha lipoic free acid (hereinafter "ALFA") of the invention has not been definitively determined, and not to be limited by theory, is believed that it is a condensation product between two or more lipoic acids via sulfide bonds, thereby forming disulfides amongst two or more individual alpha lipoic acid units. ALFA can be associated with at least one counterion, such as a metal salt, an amine or an amino acid, as well as others described infra to form an ALAC. Likewise, ALAC's can have the counterion replaced with a hydrogen atom to form ALFA.

Not to be limited by theory, it is possible that the ALFA's of the invention further include condensation products of alpha lipoic acid that are "polymeric". That is, the condensation of greater than 50 alpha lipoic acid units result from a material that is bonded via multiple disulfide linkages amongst 50 or more individual alpha lipoic acid subunits.

In one aspect, the amount of polymeric ALFA is less than 10% (by weight), more particularly, less than 1%, even more particularly less than 0.5% and in a particular embodiment, less than 0.1% by weight.

The ALAC's and ALFA of the invention can be purified by various methods described herein. That is, after the oligomerization/polymerization process, the resultant oligomer can be isolated and purified by removal of lipoic acid, lipoic acid polymer, undesired by-products, etc. by washing the material, recrystallization, precipitation, ultrafiltration with molecular weight cut off, diafiltration, etc.

In one aspect, the invention pertains to compositions that include a complex of oligomeric alpha lipoic acid and one or more counterions. The complex can be a salt, an association between the oligomeric alpha lipoic acid and the counterion and/or a chelate between two or more alpha lipoic acid molecules and at least one counterion.

In another aspect, the present invention provides compositions that include an oligomeric alpha lipoic acid complex (ALAC) comprising formula (I):

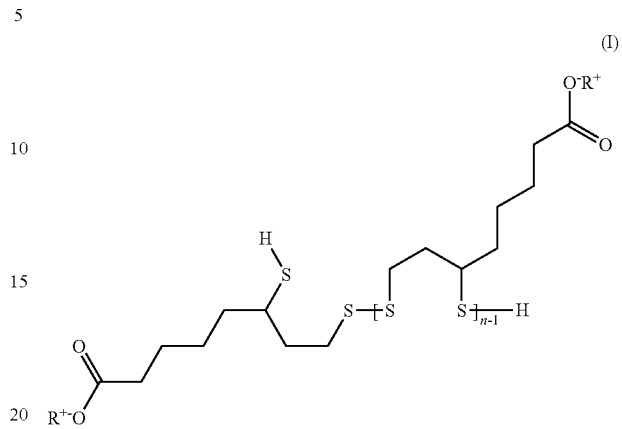

wherein each $R^+$ independently denotes a counterion, and n is a value between about 2 to about 50, in particular between about 10 and about 20, and in particular about 4 to about 6.

In one aspect, each $R^+$ is the same. In another aspect, $R^+$ can be two or more different counterions.

In still yet another embodiment, the present invention provides compositions that include a complex of an oligomeric alpha lipoic acid (ALAC) with an average (Mw) molecular weight of between about 412.6 (n=2) and about 10268.5 (n=50) daltons and a counterion(s).

In another aspect, the present invention provides oligomeric alpha lipoic acid complexes prepared by reacting a base with lipoic acid in an aqueous solution;

maintaining the solution at an elevated temperature for a period of between about 1 to about 5 hours; and precipitating a complex of the oligomeric lipoic acid and base counterion from the aqueous solution by addition of a non-solvent.

In one embodiment, the oligomeric lipoic acid complex is isolated by collecting the precipitated complex.

In certain aspects, the ALAC has a purity of greater than about 90%, more particularly greater than about, 95%, even more particularly great than about 98% and most particularly greater than about 99% (by weight), e.g., 99.5%, 99.9%, based on multiple subunits of alpha lipoic acid and one or more counterions (without contaminants from the oligomerization process).

Suitable counterions useful with the compositions of the invention include, for example, an alkali metal, alkaline earth metal, ammonium ion, an amino acid, an alkylenediamine, a monosubstituted amine, a disubstituted amine, or a trisubstituted amine.

In one aspect, the counterion is an amino acid which can include ornithine, arginine, lysine or mixtures thereof.

In another aspect, the present invention also provides compositions that include an oligomeric alpha lipoic acid free acid (ALFA) comprising formula (Ia):

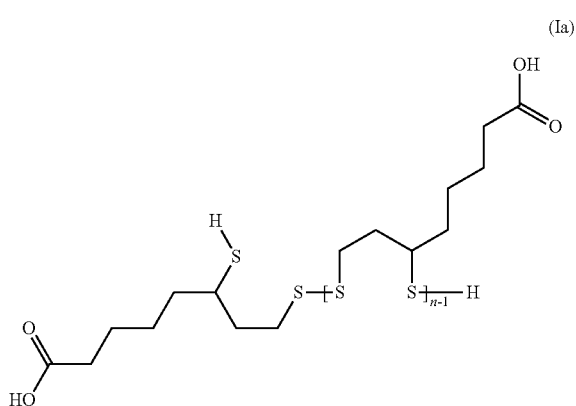

(Ia)

wherein n is a value between about 2 to about 50, in particular between about 10 and about 20, and in particular about 4 to about 6.

In still yet another embodiment, the present invention provides compositions that include oligomeric alpha lipoic free acid (ALFA) with an average (Mw) molecular weight of between about 412.6 (n=2) and about 10268.5 (n=50) daltons.

In another aspect, the present invention provides methods to prepare oligomeric alpha lipoic acid free acid.

In one embodiment, the oligomeric lipoic free acid is isolated by collecting the precipitated oligomer.

In certain aspects, the ALFA has a purity of greater than about 90%, more particularly greater than about, 95%, even more particularly great than about 98% and most particularly greater than about 99% (by weight), e.g., 99.5%, 99.9%, based on multiple subunits of alpha lipoic acid (without contaminants from the oligomerization process).

Interestingly, the compositions of the invention (ALACs and/or ALFA) can further include lipoic acid or a salt of alpha lipoic acid, which can in turn be an amino acid salt. Suitable amino acids include, for example ornithine, arginine, lysine or mixtures thereof.

In certain aspects, the compositions of the invention, with or without salts of alpha lipoic acid, have a melting point between about 165° C. and about 170° C.

In other aspects, the compositions of the invention, with or without a salt of alpha lipoic acid, have a pH value of about 7.5 when 0.5 grams of the material is dissolved in 20 ml neutral water.

The compositions of the invention can be of a solid form including granules, crystals, powders, etc.

The compositions of the invention can also include a liquid carrier.

The compositions of the invention can in particular provide oligomers of alpha lipoic acid that have an R configuration, an S configuration, a combination of R and S configurations such that the optical activity is not racemic but less than a pure R or S oligomer and also racemic mixtures.

The compositions of the invention can be used to pharmaceutical or nutraceutical preparations.

The compositions of the invention can further be used for treatment of inflammation, as antioxidants, for treatment of circulatory disorders. as analgesics, as antinecrotics, and for treatment of retroviral diseases.

The compositions of the invention can also be used to help stabilize nutritional substances that otherwise are unstable at ambient conditions.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1:
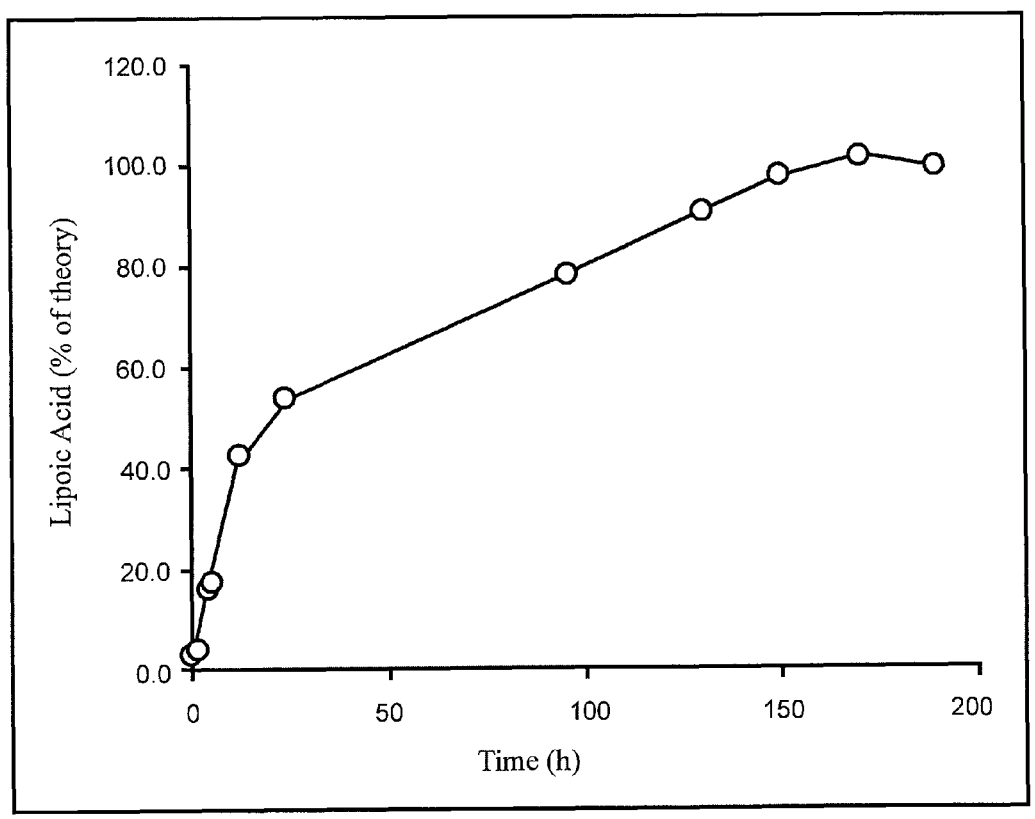
FIG. 1 demonstrates the liberation of lipoic acid from LAORN after dissolution in water over time.

The present invention surprisingly provides complexes of alpha lipoic acid that are oligomeric. The exact nature of the alpha lipoic acid complexes ("ALAC") of the invention have not been definitively determined, and not to be limited by theory, is believed that they are condensation products between two or more lipoic acids via sulfide bonds, thereby forming disulfides amongst two or more individual alpha lipoic acid units. The ALAC can be associated with at least one counterion, such as a metal salt, an amine or an amino acid, as well as others described infra.

Again, not to be limited by theory, it is possible that the ALAC's of the invention further include complexes of alpha lipoic acid that are "polymeric". That is, the condensation of more than about 50 alpha lipoic acid units result from a material that is bonded via multiple disulfide linkages amongst 50 or more individual alpha lipoic acid subunits.

In one aspect, the invention pertains to compositions that include a complex of oligomeric alpha lipoic acid and one or more counterions. The complex can be a salt, an association between the oligomeric alpha lipoic acid and the counterion and/or a chelate between two or more alpha lipoic acid molecules and at least one counterion.

In another aspect, the invention pertains to oligomeric alpha lipoic acid as the "free acid" (ALFA).

In another aspect, the invention pertains to mixtures of ALFA and one or more ALACs.

In still another embodiment, the ALAC can be only partially complexed; meaning that there can be a portion of the oligomer that is protonated and a portion that is complexed with one or more counterions. This is depicted below in Formula II.

The terms "alpha lipoic acid" and "lipoic acid" are used interchangeably herein and refer to thioctic acid, 1,2-dithiolane-3-pentanoic acid, 1,2-dithiolane-3-valeric acid and 6,8-thioctic acid as are commonly known in the art. It should be understood that throughout this application, the term "alpha lipoic acid" is intended to include any isomer of lipoic acid and is not meant to be limiting.

The term "oligomeric" is intended to include materials that have at least 2 subunits of, for example, alpha lipoic acid, that have condensed in some fashion to product a material that has a molecular weight greater than alpha lipoic acid per se. Generally, oligomers of the invention will have between about 2 and about 50 subunits of alpha lipoic acid contained within the oligomeric structure.

Interestingly, the "oligomeric" ALACs and ALFA of the invention degrade over time under physiological conditions such as those in the stomach or the ileum. However, it has been found that "polymeric" ALFA in particular does not readily degrade in similar environments. This differentiation makes it possible to use the oligomers of the invention to deliver nutritional components as well as provide a beneficial effect of the lipoic acid itself upon it's degradation, especially if the lipoic acid derivative is an ALAC, such as an amino acid complex.

The term "polymeric alpha lipoic acid" is intended to include those materials that have more than 50 subunits of alpha lipoic acid within the molecule.

The phrase "salt of alpha lipoic acid" or "salt of lipoic acid" is intended to mean an acid base reaction between a lipoic acid molecule and a base molecule, such that a counterion become associated with the carboxylic acid of the alpha lipoic acid.

The term "free acid" is intended to mean that the carboxylic acid portion of the oligomerized lipoic acid, for example, is protonated.

The term "complex" as used herein is intended to mean an association between a counterion and a molecule, such as the carboxylic acid of an alpha lipoic acid. The association can be ionic, covalent, van der Waals interactions, and/or by chelation, etc. The term is intended to mean that there is a physical attraction between the ion, (anions and cations), such as a carboxyl group and the counterion, such as a salt or an amino acid.

It should be understood that acceptable salts include salts formed when an acidic proton present in the parent compound, alpha lipoic acid for example, is either replaced by a metal ion (e.g., an alkali metal ion, an alkaline earth metal ion or an aluminum ion) or coordinates with an organic base (e.g., ethanolamine, diethanolamine, triethanolamine, N-methylglucamine, morpholine, piperidine, dimethylamine, diethylamine, etc.). Also included are salts of amino acids such as arginates and the like, and salts of organic acids like glucurmic or galactunoric acids and the like (see, e.g., Berge et al., 1977, *J. Pharm. Sci.* 66:1-19).

"Pharmaceutically acceptable salts" are also included as suitable counterions and refers to the relatively non-toxic, inorganic and organic base addition salts of compounds of the present invention. These salts can be prepared in situ during the final isolation and purification of the compounds, or by separately reacting the purified compound (ALFA) in its free acid form with a suitable base, such as the hydroxide, carbonate or bicarbonate of a metal cation, with ammonia, or with a pharmaceutically-acceptable organic primary, secondary, tertiary or quaternary amine. Representative alkali or alkaline earth salts include the lithium, sodium, potassium, calcium, magnesium, and aluminum salts and the like. Representative organic amines useful for the formation of base addition salts include ethylamine, tetramethyl-ammonium hydroxide, diethylamine, ethylenediamine, ethanolamine, diethanolamine, piperazine and the like. (See, for example, S. M. Berge et al., "Pharmaceutical Salts," supra.)

The term "alkali metal ion" is intended to mean those elements in group Ia of the periodic table, with the exception of hydrogen.

Suitable alkali metal ions include, for example, sodium and potassium ions.

The term "alkaline earth metal ion" is intended to mean Group 2 (IIA) elements of the periodic table.

Suitable alkaline earth metal ions include, for example, magnesium and calcium.

Other suitable ions include, for example, aluminum, zinc, copper, or iron.

The term "amino acid" as used herein includes, but is not limited to, the enantiomers and racemic mixtures of glycine, alanine, valine, leucine, isoleucine, phenylalanine, tyrosine, proline, hydroxyproline, serine, threonine, cysteine, cystine, methionine, tryptophan, aspartic acid, glutamic acid, arginine, lysine, histidine, ornithine, hydroxylysine, carnitine, and other naturally occurring amino acids and analogs thereof. In one embodiment, the amino acid is in the "L" form.

For example amino acid analogs, such as ornithine "analogs" include acetylated products, fumarate derivatives and the like, and acceptable ammonium and metal salts thereof.

The term "monosubstituted amine" is intended to mean an amine having a single substituent on the amine nitrogen. The substituent can be an alkyl or an aryl group.

Suitable monosubstituted amines include, for example, methylamine, ethylamine, phenylamine and the like.

The term "dialkyl substituted amine" is intended to mean an amine having two substituents on the amine nitrogen. The substituents can be alkyl groups, aryl groups or combinations thereof.

Suitable dialkyl substituted amines include, for example, diethylamine, dimethylamine, diphenylamine and the like.

The term "trialkyl substituted amine" is intended to mean an amine having three substituents about the amine nitrogen. The substituents can be alkyl groups, aryl groups or combinations thereof.

Suitable trialkyl substituted amines include, for example, trimethylamine, triethylamine, triphenylamine and the like The term "alkylenediamine" is intended to mean those compounds having two amines within the carbon skeleton. The amines can be at the terminus or within the carbon skeleton.

Suitable alkylenediamines include, for example, ethylenediamine or hexamethylene tetramine.

Alkyl groups can include straight-chained, branched and cyclic alkyl radicals containing up to about 20 carbons. Suitable alkyl groups may be saturated or unsaturated. Further, an alkyl may also be substituted one or more times on one or more carbons with one or more substituents selected from the group consisting of C1-C6 alkyl, C3-C6 heterocycle, aryl, halo, hydroxy, amino, alkoxy and sulfonyl. Additionally, an alkyl group may contain up to 10 heteroatoms or heteroatom substituents. Suitable heteroatoms include nitrogen, oxygen, sulfur and phosphorous.

Aryl groups are aryl radicals which may contain up to 10 heteroatoms. An aryl group may also be optionally substituted one or more times with an aryl group or a lower alkyl group and it may be also fused to other aryl or cycloalkyl rings. Suitable aryl groups include, for example, phenyl, naphthyl, tolyl, imidazolyl, pyridyl, pyrroyl, thienyl, pyrimidyl, thiazolyl and furyl groups.

The term "ring" is defined as having up to 20 atoms that may include one or more nitrogen, oxygen, sulfur or phosphorous atoms, provided that the ring can have one or more substituents selected from the group consisting of hydrogen, alkyl, allyl, alkenyl, alkynyl, aryl, heteroaryl, chloro, iodo, bromo, fluoro, hydroxy, alkoxy, aryloxy, carboxy, amino, alkylamino, dialkylamino, acylamino, carboxamido, cyano, oxo, thio, alkylthio, arylthio, acylthio, alkylsulfonate, arylsulfonate, phosphoryl, and sulfonyl, and further provided that the ring may also contain one or more fused rings, including carbocyclic, heterocyclic, aryl or heteroaryl rings.

The term "alkylene" refers to a straight, branched or cyclic, in certain embodiments straight or branched, divalent aliphatic hydrocarbon group, in one embodiment having from 1 to about 20 carbon atoms, in another embodiment having from 1 to 12 carbons. In a further embodiment alkylene includes lower alkylene. There may be optionally inserted along the alkylene group one or more oxygen, sulfur or substituted or unsubstituted nitrogen atoms, where the nitrogen substituent is alkyl. Alkylene groups include, but are not limited to, methylene (—$CH_2$—), ethylene (—$CH_2CH_2$—), propylene (—$(CH_2)_3$—), methylenedioxy (—O—$CH_2$—O—) and ethylenedioxy (—O—$(CH_2)_2$—O—). The term "lower alkylene" refers to alkylene groups having 1 to 6 carbons. In certain embodiments, alkylene groups are lower alkylene, including alkylene of 1 to 3 carbon atoms.

The term "weight average molecular weight" (Mw) is recognized in the art and the weight average molecular weight can be determined by light scattering, small angle neutron scattering (SANS), X-ray scattering, sedimentation velocity, iodiometry, or by gel permeation chromatography (GPC). The Mw of the oligomeric ALAC(s) and ALFA are generally from about 412.6 (n=2) to about 10268.5 (n=50), more particularly from about 412.6 (n=2) to about 3081.95 (n=15), and still more specifically from about 412.6 (n=2) to about 2055.3 (n=10) and still more specifically from about 412.6 (n=2) to about 1233.98 (n=6).

In another aspect, the present invention provides compositions that include an oligomeric alpha lipoic acid complex comprising formula (I):

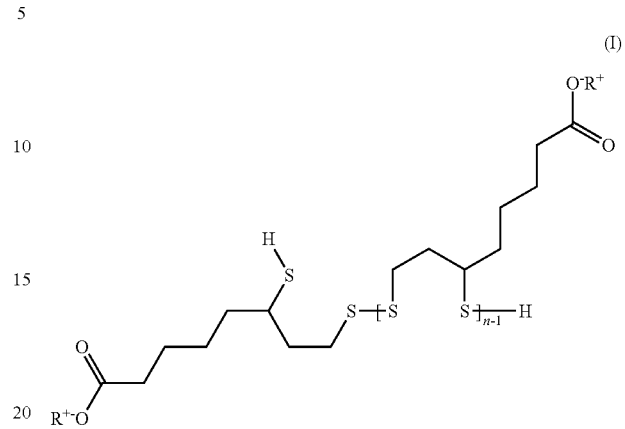

wherein each $R^+$ independently denotes a counterion, and n is a value between about 2 to about 50, in particular between about 4 and about 20, in particular about 10 to about 15, and in particular about 4 to about 12, e.g., about 4, about 6, about 8, about 10, or about 12.

It should be understood that each $R^+$ can be the same or the $R^+$'s in the oligomer can have different counterions.

For example, if the degree of oligomerization n is 2, the structure of the compound according to the present invention is believed to be as follows:

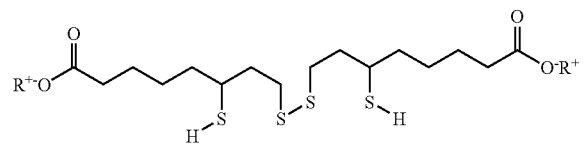

wherein each $R^+$, individually, is defined as above.

If the degree of oligomerization n is 3, the structure of the compound according to the present invention is believed to be as follows:

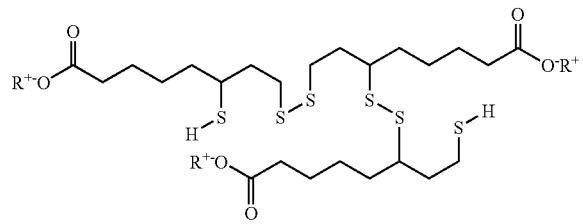

wherein each $R^+$, individually, is defined as above.

The repeating chain of alpha lipoic acid subunits can be prolonged by more units (n=2, 3, 4, 5, 6, 7, 8, 9, 10, 11, 12, 13, 14, 20, etc. up to and including 50, respectively). The final structure will depend on where (i.e. at which sulfide group) further oligomerization takes place. It should further be understood that the value can be a non-integer as the molecular weight distribution is an average, therefore, fractions of whole values (integers) are also contemplated and included.

It should be understood that throughout the specification that the compositions of the invention can be present as a mixture of compounds having a different degree of oligomerization, n, respectively, and can further include monomeric complexes or salts of alpha lipoic acid.

It should also be understood that one or more of the $R^+$ can be replaced by a hydrogen atom to provide, for example, ALFA (where all $R^+$ are hydrogen).

In still yet another embodiment, the present invention provides compositions that include a complex of an oligomeric alpha lipoic acid with an average (Mw) molecular weight of between about 412.6 (n=2) and about 10268.5 (n=50) daltons and a counterion(s).

In another aspect, the present invention also provides compositions that include an oligomeric alpha lipoic acid free acid (ALFA) comprising formula (Ia):

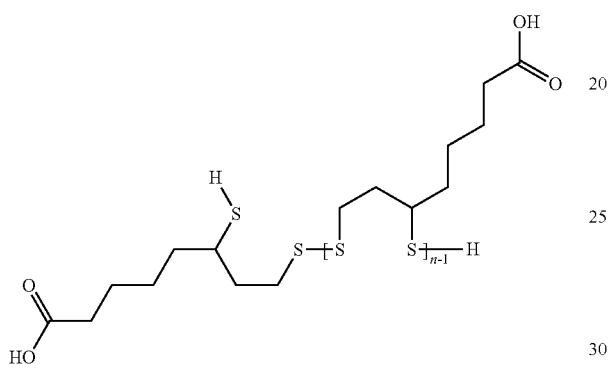

(Ia)

wherein n is as described above and is a value between about 2 to about 50, in particular between about 10 and about 20, and in particular about 4 to about 6.

In still yet another embodiment, the present invention provides compositions that include oligomeric alpha lipoic free acid (ALFA) with an average (Mw) molecular weight of between about 412.6 (n=2) and about 10268.5 (n=50) daltons.

In another aspect, the present invention also provides compositions that include a mixed oligomeric alpha lipoic acid complex comprising formula (II):

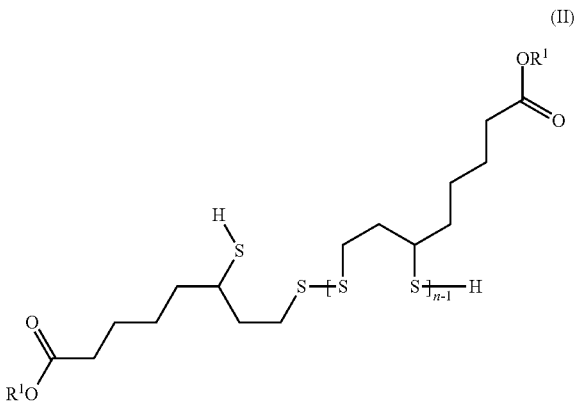

(II)

wherein n is as described above;
each $R^1$ independently is a hydrogen atom or counterion provided at least one $R^1$ is a counterion.

In still another aspect, the present invention also provide compositions that include alpha lipoic acid oligomers comprising formula (III):

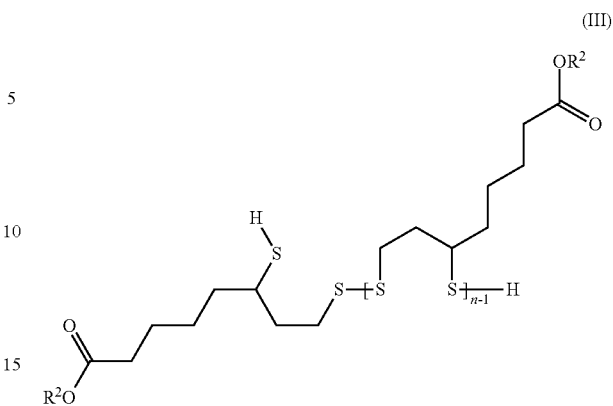

(III)

wherein n is as described above;
each $R^2$ independently is a hydrogen atom or a counterion. When all $R^2$'s are hydrogen atoms, the result is ALFA.

The present invention provides methods to prepare an oligomeric lipoic acid complex by contacting lipoic acid with a base to form a mixture; heating the mixture at a temperature between about 0° C. and about 100° C.; and collecting the oligomeric lipoic acid complex, wherein the degree of polymerization of the lipoic acid is between about 2 and about 50, e.g., between about 4 and about 20.

In certain aspects, 1 molar equivalent of base is added per molar equivalent carboxylic acid. In other aspects, less than 1 molar equivalent of base is added per molar equivalent carboxylic acid, thereby providing a "mixed" ALAC.

In another aspect, the present invention provides products produced by the process of:

a) reacting a base with alpha lipoic acid in an aqueous solution;

b) maintaining the solution at an elevated temperature for a period of between about 1 to about 5 hours; and either c) precipitating a complex of the oligomeric lipoic acid and base counterion from the aqueous solution by addition of a non-solvent or spray drying the solution to afford the oligomeric lipoic acid salt complex.

In one embodiment, the oligomeric lipoic acid complex is isolated by collecting the precipitated complex.

Generally the oligomerization reaction is conducted in a temperature range of between about 0° C. and about 100° C., more particularly between about 30° C. and about 60° C. An excess of base can be present during the reaction and any excess unreacted base or uncomplexed base can be removed upon purification. It has been found that conducting the reaction under alkaline conditions provides for oligomerization reactions that occur in lower temperature ranges, such as between about 30° C. and about 60° C. and provides good yields of the oligomerized ALACs.

Surprisingly, it has been found that when reacting a base such as an amino acid and α-lipoic acid in an aqueous solution and keeping the solution at an elevated temperature for a period as defined above, an oligomeric complex results.

The base is generally an amino acid employed in step a) and is selected from ornithine, arginine and lysine. The amino acid is preferably provided in its L-form, although the R-form is also possible. Most preferably, L-ornithine is used as the base.

In one embodiment, if ornithine is employed in step a), it is provided in the form of an aqueous solution with a pH-value of from about 9.5 to about 10.0, e.g., 9.6. In this range of pH-values, which are close to the iso-electric point of ornithine (9.6), ornithine will be present in a form with one positive charge and, hence, can form a salt complex with the α-lipoic acid which exhibits one negative charge.

In one exemplary embodiment, the aqueous solution of ornithine employed in step a) may be produced by adding NaOH to a solution containing the hydrochloride salt of ornithine until the desired pH-value is obtained.

The α-lipoic acid employed in step a) can be provided in its R(+)-form, S(−)-form or in racemic form.

Step b) can include the step of concentrating the aqueous solution. For example, the reaction mixture can be concentrated towards the end of step b) until about 50% of the water is removed.

It has been found that the oligomerization of the α-lipoic acid employed in the process according to the invention is, in addition to the treatment at elevated temperature, to some degree dependent on the sum of the concentrations of the two reactant in the reaction mixture. In one embodiment, the sum of the respective concentrations of the base, e.g., an amino acid such as ornithine and α-lipoic acid in the aqueous solution in step a) is from about 15% to about 45% (w/v), and more particularly from about 25% to about 35% (w/v) (weight to volume, mg/ml) with molar ratios of the amino acid to lipoic acid within the range of 0.1:1 to 10:1. Although the oligomerization can be more pronounced at higher concentrations, the higher viscosities of the resulting reaction mixture make it more difficult to work with.

Generally, the molar ratio of base, e.g., an amino acid and α-lipoic acid in step a) of the process is about 1:1.

The temperature of the reaction mixture in step b) is about 30° C. or higher, and in particular from about 40° C. to about 50° C. In this regard, lower temperatures appear to promote oligomerization, however, temperatures below 30° C. are not as desirable as the viscosity of the reaction mixture increases and makes handling more difficult but not impossible.

The non-solvent used in step c) can be an alcohol and in one embodiment is an ethanolic solution.

The water content of the mixture of the aqueous solution and the non-solvent (e.g., ethanolic) solution used for precipitating the ALAC in step c) should generally be 12% or less. If the water content of the solution is much higher, the precipitated complex tends to be sticky and drying tends to be difficult. However, if the water content is too low, then an increased percentage of non-solvent, such as ethanol, is generally required, which can increase the production costs. In one embodiment, a final ethanol content of 88% has been found to be both economical and beneficial in terms of the yield and the purity of the end product.

The ALAC, whether it be oligomeric and whether the complex is a salt, a loosely associated anion-cation complex, a chelate or some other association, are very heat stable as compared with α-lipoic acid. The ALAC's of the invention possess a surprisingly high antioxidative effect.

Furthermore, the ALAC's of the invention appear to release α-lipoic acid in a relatively equal amount over time, i.e. therefore, it can be used as a "controlled release" product having α-lipoic acid-like effect.

In contrast to α-lipoic acid, the ALAC's do not cause irritation of the throat when administered perorally as alpha-lipoic acid can cause.

The ALAC's of the invention possess favourable gelling properties, therefore the need for a binding agent for making tablets can be reduced or even eliminated. In contrast thereto, α-lipoic acid can not be compressed into tablets due to its low melting point.

ALFA can be prepared by dissolving lipoic acid in an alcohol, such as ethanol, and heating the solution to temperature of between about 30° C. and about 60° C. Upon cooling, depending upon the alcohol or solvent chosen, a yellow precipitate will form from the solution and can be collected, isolated, and purified further if required. Oligomerized ALFA is not water soluble, so water can be used to remove any unwanted water soluble materials. Alternatively, the solution can be spray dried to afford the ALFA, generally having a degree of polymerization of about 3 to about 4.

ALFA is very heat stable as compared with α-lipoic acid. ALFA of the invention possess a surprisingly high antioxidative effect.

Furthermore, ALFA of the invention appears to release α-lipoic acid in a relatively equal amount over time, i.e. therefore, it can be used as a "controlled release" product having α-lipoic acid-like effect.

In contrast to α-lipoic acid, the ALFA does not cause irritation of the throat when administered perorally as alpha-lipoic acid can cause.

ALFA of the invention possesses favourable gelling properties, therefore the need for a binding agent for making tablets can be reduced or even eliminated. In contrast thereto, α-lipoic acid can not be compressed into tablets due to its low melting point.

In one aspect the ALACs and/or ALFA of the invention can be combined with nutritional materials that are unstable to heat, light, oxygen and other environmental stresses such as humidity, ozone, etc. The ALAC and/or ALFA can be coated onto the nutritional material (such as a carotenoid and their derivatives, such as esters, including for example, palmitic acid, citric acid, gallic acid, vitamin E, lipoic acid esters) or intimately mixed with the nutritional material to help stabilize the material.

It should be understood that coating the nutritional component can be accomplished by methods known in the art such as by simply dipping the nutritional component in a solution of the ALAC and/or ALFA, spray drying the material in combination with the ALAC and/or ALFA, lyophilizing nutritional component with the ALAC and/or ALFA, etc. It should also be understood that the coating does not have to be completely uniform about the nutritional material, although in certain instances a uniform coating is preferred.

Carotenoids are yellow, red and orange pigments that are widely distributed in nature. Although specific carotenoids have been identified in various fruits and vegetables, bird feathers, egg-yolk, poultry skin, crustaceans and macular eye region, they are especially abundant in marigold petals, corn and leafy vegetables. The correlation between dietary carotenoids and carotenoids found in human serum and plasma indicate that only selected groups of carotenoids make their way into the human blood stream to exert their effect.

Carotenoids absorb light in the 400-500 nm region of the visible spectrum. This physical characteristic imparts the yellow/red color to the pigments. Carotenoids contain a conjugated backbone composed of isoprene units, which are usually inverted at the center of the molecule, imparting symmetry. Changes in geometrical configuration about the double bonds result in the existence of many cis- and trans-isomers. Mammalian species do not synthesize carotenoids and therefore these have to be obtained from dietary sources such as fruits, vegetables and egg yolks. In the recent years, carotenoids have been attributed several health benefits, which include prevention and or protection against serious health disorders.

Carotenoids are non-polar compounds classified into two sub-classes, namely more polar compounds called xanthophylls or oxy-carotenoids and non-polar hydrocarbon carotenes like [beta]-carotene, lycopene, etc. Both the sub-classes have at least nine conjugated double bonds responsible for the characteristic color of the carotenoids. Xanthophylls have ring structures at the end of the conjugated double bond chain with polar functionalities, such as hydroxyl or keto groups. Examples of xanthophylls include lutein, zeaxanthin, capsanthin, canthaxanthin, β-cryptoxanthin, astaxanthin, etc. As natural colorants and also for their role in human health, xanthophylls containing lutein and zeaxanthin have attracted the renewed attention of scientists and researchers in the biomedical, chemical and nutritional field in recent years.

Lutein and zeaxanthin contribute to yellow and orange-yellow color respectively. Lutein and zeaxanthin can be present in plant material in free form (non-esterified) and also as esters. Lutein is present in green leafy vegetables like spinach, kale and broccoli in the free form while fruits like mango, orange, papaya, red paprika, algae and yellow corn. These sources generally contain lutein in the form of its esters etc. Lutein is also present in the blood stream and various tissues in human body and particularly the macula, lens and retina of the eye.

Therefore, it should be understood that the present invention includes the use of the various ALACs and ALFA to coat esterified carotenoids, also referred to as derivatives of carotenoids, as well as non-esterified carotenoids. Common acids that are often associated with the non-esterified carotenoid to afford the esterified carotenoid include, for example, palmitic acid, citric acid, gallic acid, vitamin E, lipoic acid, etc. that are known in the art.

Essentially, lutein esters and lutein in the free form are commercially important nutraceuticals obtained from marigold flowers. Dried flowers are used for obtaining marigold extract or oleoresin. By subjecting the extract/oleoresin to saponification, xanthophylls in the free form are obtained. The resultant alkali salts of fatty acids obtained from the saponification are removed and the xanthophyll containing mixture of lutein and zeaxanthin purified further.

In the fresh marigold flowers, lutein esters exist in trans-isomeric form, whereas exposure to heat, light, oxygen, acid, etc. catalyses isomerization from trans- to cis-lutein geometric isomeric forms. As a nutraceutical and food additive, the trans-isomeric form of lutein is preferred because of better bio-availability and deeper yellow color compared to the corresponding cis-isomeric form.

In particular, carotenoids are a class of hydrocarbons (carotenes) and the corresponding oxygenated derivatives are xanthophylls. They consist of eight isoprenoid units joined in such a manner that the arrangement of isoprenoid units is reversed at the center of the molecule so that the two central methyl groups are in a 1,6-position relationship and the remaining nonterminal methyl groups are in a 1,5-position relationship. All carotenoids may be formally derived from the acyclic $C_{40}H_{56}$ structure (I) (Compound I), having a long central chain of conjugated double bonds, by (1) hydrogenation, (2) dehydrogenation, (3) cyclization, or (4) oxidation, or any combination of these processes. The class also includes compounds that arise from certain rearrangements or degradations of the carbon skeleton (I) (lycopene), provided that the two central methyl groups are retained.

I

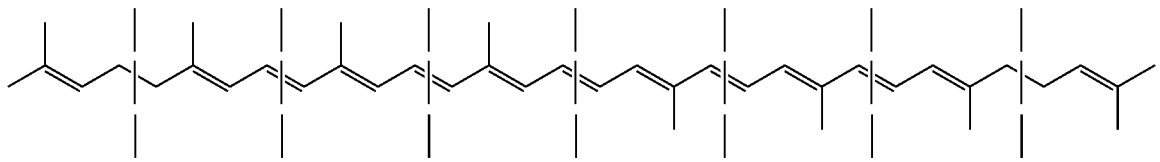

Marigold (*Tagetes erecta*) flower petals are a rich source of lutein in its esterified form. The ester portion(s) are fatty acids. Dried marigold flowers contain approximately 1-1.6% carotenoids by weight and lutein esters content accounts for 90% of the total carotenoids. The xanthophyll fatty acid esters composition in marigold oleoresin chiefly consists of lutein in its ester form as di-palmitate, myristate-palmitate, palmitate-stearate, dimyristate and monoesters.

Lutein obtained by the hydrolysis of lutein esters from marigold have been found to be identical to the lutein found in fruits, vegetables and in human plasma and the macular region. After absorption, the human body cannot distinguish the source of lutein. Therefore, a widely cultivated and commercially processed raw material like marigold, which is already used by the food and feed industry, is an attractive source for lutein in view of abundant availability and cost considerations.

About 600 carotenoids have been isolated from natural sources. These carotenoids have been listed with their trivial and semisystematic names in Key to Carotenoids (Pfander, 1987) and in the Appendix of Carotenoids, Volume 1A (Kull & Pfander 1995) which also includes literature references for their spectroscopic and other properties. The structure is still uncertain for many of the carotenoids, including stereochemical assignments. In the cases where the structure is uncertain, resolution, followed by structural elucidation with modern spectroscopic methods (including high resolution nuclear magnetic resonance (NMR) spectroscopy) is necessary. About 370 of the naturally occurring carotenoids are chiral, bearing from one to five asymmetric carbon atoms, and in most cases one carotenoid occurs only in one configuration in Nature.

All specific names of carotenoids are based on the stem name carotene, which corresponds to the structure and numbering as in Compound 2 (carotene).

II

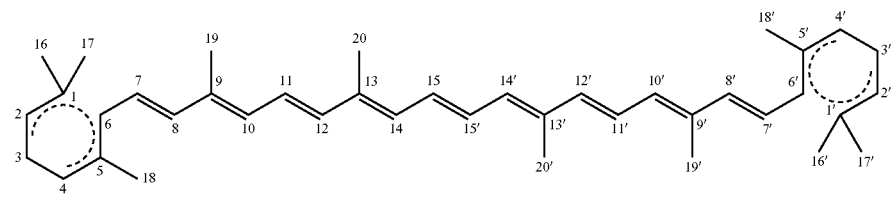

The name of a specific compound is constructed by adding two Greek letters as prefixes (Compound fragments 3) to the stem name carotene. The Greek letter prefixes are cited in alphabetical order noted in compounds IIa.

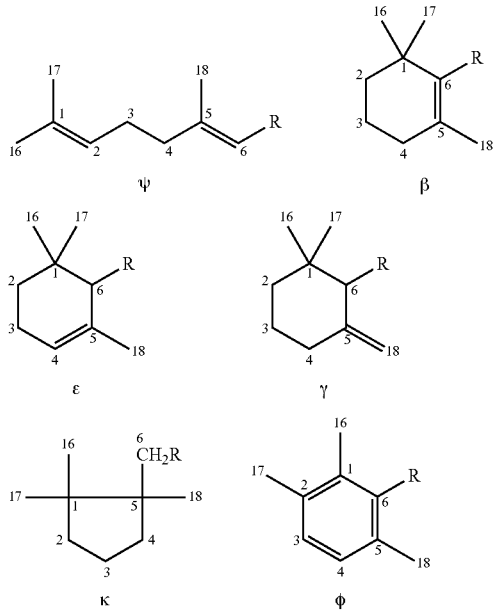

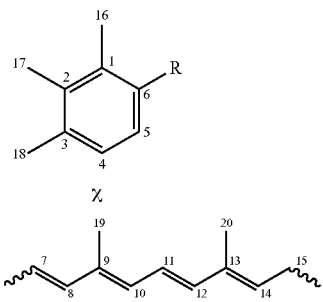

The oxygenated carotenoids (xanthophylls) most frequently include hydroxy, methoxy, carboxy, oxo, and epoxy functionality. Important and characteristic carotenoids (Compounds III through X) are lycopene (gamma, gamma-carotene) (I), beta-carotene (beta, beta-carotene) (III), alpha-carotene ((6'R)-beta, epsilon-carotene) (IV), beta-cryptoxanthin ((3R)-beta,beta-caroten-3-ol) (V), zeaxanthin ((3R,3'R)-beta, beta carotene-3,3'-diol) (VI), lutein ("xanthophyll", (3R,3'R,6'R)-beta, epsilon-carotene-3,3'-diol) (VII), neoxanthin ((3S,5R,6R,3'S,5'R,6'S)-5',6'-epoxy-6,7-didehydro-5,6, S',6'-tetrahydro-beta,beta-carotene-3,5,3'-triol) (VIII), violaxanthin ((3S,5R,6R,3'S,5'R,6'S)-5,6,5',6'-diepoxy-5,6,5', 6'-tetrahydro-beta,beta-carotene-3,3'-diol) (IX), fucoxanthin ((3S,5R,6S,3'S,5'R,6'R)-5,6-epoxy-3,3',5'-trihydroxy-6',7'-didehydro-5,6,7,8,5',6'-hexahydro-beta,beta-caroten-8-one 3'-acetate) (X), canthaxanthin (beta,beta-carotene-4,4'-dione) (XI), and astaxanthin ((3S,3'S)-3,3'-dihydroxy-beta, beta-carotene-4,4'-dione) (XII).

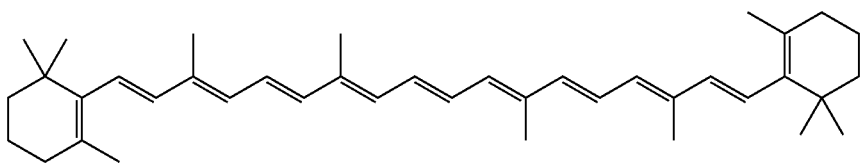

III

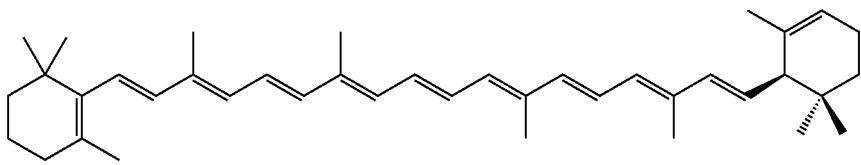

IV

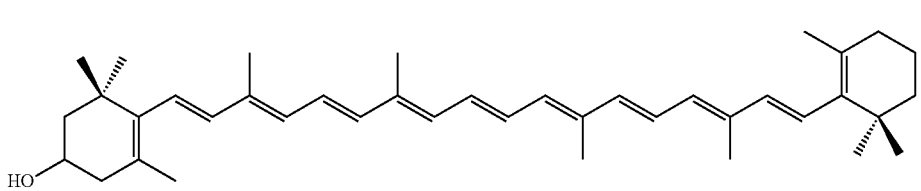

V

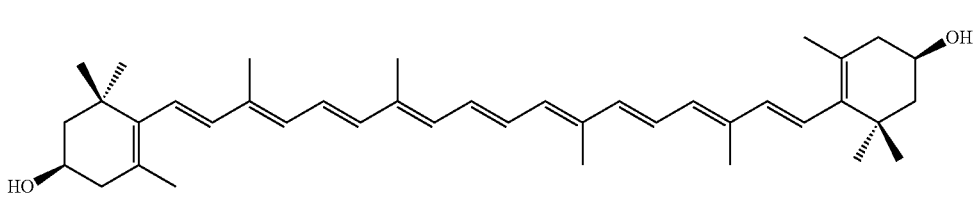

VI

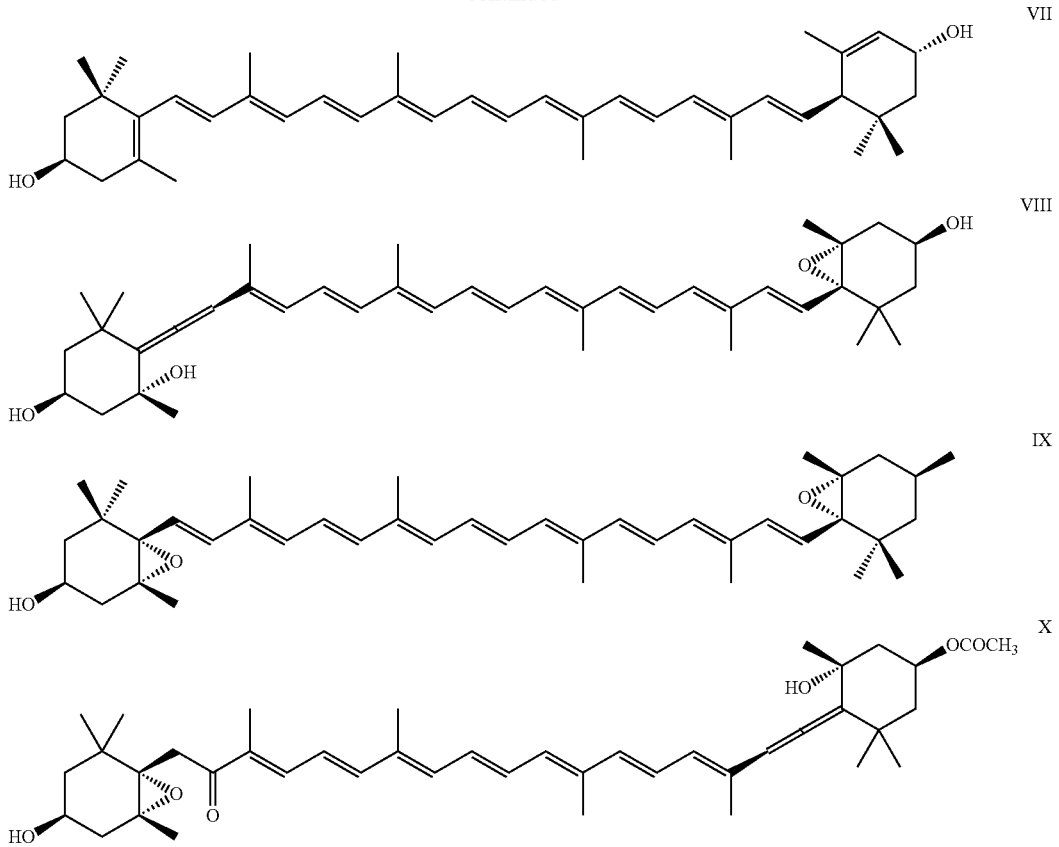

Normally carotenoids occur in Nature as the (all-E)-isomer. Some carotenoids undergo isomerization very easily during processing. For processing, it must be kept in mind that (E/Z)-isomerization can occur when a carotenoid is kept in solution. Normally the percentage of the (Z)-isomers is rather low, but it is enhanced at higher temperatures. Furthermore, the formation of (Z)-isomers is increased by exposure to light.

In commercial practice, xanthophylls of food grade quality and free of Z-lutein isomers are seldom achieved because of lack of selectivity in the raw material and improper processing conditions including high temperature drying. This results in the formation of xanthophylls of food grade quality but having higher levels of Z-lutein. The present invention avoids such increased levels of undesired Z-lutein, in part because of the relatively low temperatures used in the processes.

Humans and animals cannot synthesize xanthophylls like lutein and zeaxanthin, and the source of this has to be from diet. The occurrence of lutein and zeaxanthin in the macula has specific functions, viz., protection of the cells and tissues from ultra-violet light and reduced cataract risk. Lutein and zeaxanthin are known to comprise the macular pigment and lutein isomerizes into zeaxanthin in the macula.

There is evidence suggesting that lutein may have a protective effect against cancers of the breast, colon, lung, skin, cervix and ovaries and could bear promise in treatment of cardiovascular disease. Therefore, providing lutein to an individual for use in their diet or as nutritional supplements supports better human health and healthy vision.

Therefore, there is a high demand for xanthophyll crystals containing high amounts of trans (E)-lutein and/or zeaxanthin for its use as antioxidants, prevention of cataract and macular degeneration, as lung cancer-preventive agents, as agents for the absorption of harmful ultra-violet light from the rays of the sun and quencher of photo-induced free radical and reactive oxygen species, etc.

Consequently, the combination of one or more ALACs and/or ALFA of the invention provide a carotenoid that is stabilized to typical degradation. The invention, therefore, provides a method to help stabilize carotenoids, such as lutein.

The compositions of the invention can be incorporated into various foods, drinks, snacks, etc. In one aspect, the composition can be sprinkled onto a food product, prior to consumption. If sprinkled onto a food product, a suitable carrier such as starch, sucrose or lactose, can be used to help distribute the concentration of the compositions making it easier to apply to the food product.

The compositions of the present invention can also be provided as supplements in various prepared food products. For the purposes of this application, prepared food product means any natural, processed, diet or non-diet food product to which a composition of the invention has been added. The compositions of the present invention can be directly incorporated into many prepared diet food products, including, but not limited to diet drinks, diet bars and prepared frozen meals. Furthermore, the compositions of the inventions can be incorporated into many prepared non-diet products, including, but not limited to candy, snack products such as chips, prepared meat products, milk, cheese, yogurt, sport bars, sport drinks, mayonnaise, salad dressing, bread and any other fat or oil containing foods. As used herein, the term "food product" refers to any substance fit for human or animal consumption.

The compositions of the invention can be added to various drinks, such as fruit juices, milkshakes, milk, etc.

The preferred method of administration is oral. The compositions of the invention can be formulated with suitable carriers such as starch, sucrose or lactose in tablets, capsules, solutions, syrups and emulsions. The tablet or capsule of the present invention can be coated with an enteric coating that dissolves at a pH of about 6.0 to 7.0. A suitable enteric coating, which dissolves in the small intestine but not in the stomach, is cellulose acetate phthalate.

Formulation of the compositions of the invention into a soft gel capsule can be accomplished by many methods known in the art. Often the formulation will include an acceptable carrier, such as an oil, or other suspending or emulsifying agent.

Suitable optional carriers include but are not limited to, for example, fatty acids, esters and salts thereof, that can be derived from any source, including, without limitation, natural or synthetic oils, fats, waxes or combinations thereof. Moreover, the fatty acids can be derived, without limitation, from non-hydrogenated oils, partially hydrogenated oils, fully hydrogenated oils or combinations thereof. Non-limiting exemplary sources of fatty acids (their esters and salts) include seed oil, fish or marine oil, canola oil, vegetable oil, safflower oil, sunflower oil, nasturtium seed oil, mustard seed oil, olive oil, sesame oil, soybean oil, corn oil, peanut oil, cottonseed oil, rice bran oil, babassu nut oil, palm oil, low erucic rapeseed oil, palm kernel oil, lupin oil, coconut oil, flaxseed oil, evening primrose oil, jojoba, wheat germ oil, tallow, beef tallow, butter, chicken fat, lard, dairy butterfat, shea butter or combinations thereof.

Specific non-limiting exemplary fish or marine oil sources include shellfish oil, tuna oil, mackerel oil, salmon oil, menhaden, anchovy, herring, trout, sardines or combinations thereof. In particular, the source of the fatty acids is fish or marine oil (DHA or EPA), soybean oil or flaxseed oil. Alternatively or in combination with one of the above identified carrier, beeswax can be used as a suitable carrier, as well as suspending agents such as silica (silicon dioxide).

The compositions of the invention are also considered to be nutraceuticals. The term "nutraceutical" is recognized in the art and is intended to describe specific chemical compounds found in foods that can prevent disease or ameliorate an undesirable condition.

The compositions of the invention can further include various ingredients to help stabilize, or help promote the bioavailability of the components of the beneficial compositions of the invention or serve as additional nutrients to an individual's diet. Suitable additives can include vitamins and biologically-acceptable minerals. Non-limiting examples of vitamins include vitamin A, B vitamins, vitamin C, vitamin D, vitamin E, vitamin K and folic acid. Non-limiting examples of minerals include iron, calcium, magnesium, potassium, copper, chromium, zinc, molybdenum, iodine, boron, selenium, manganese, derivatives thereof or combinations thereof. These vitamins and minerals can be from any source or combination of sources, without limitation. Non-limiting exemplary B vitamins include, without limitation, thiamine, niacinamide, pyridoxine, riboflavin, cyanocobalamin, biotin, pantothenic acid or combinations thereof.

Various additives can be incorporated into the present compositions. Optional additives of the present composition include, without limitation, hyaluronic acid, phospholipids, starches, sugars, fats, antioxidants, amino acids, proteins, flavorings, coloring agents, hydrolyzed starch(es) and derivatives thereof or combinations thereof.

As used herein, the term "antioxidant" is recognized in the art and refers to synthetic or natural substances that prevent or delay the oxidative deterioration of a compound. Exemplary antioxidants include tocopherols, flavonoids, catechins, superoxide dismutase, lecithin, gamma oryzanol; vitamins, such as vitamins A, C (ascorbic acid) and E and beta-carotene; natural components such as camosol, camosic acid and rosmanol found in rosemary and hawthorn extract, proanthocyanidins such as those found in grapeseed or pine bark extract, and green tea extract.

Compositions comprising the ALAC and/or ALFA compositions of the invention can be manufactured by methods of conventional mixing, dissolving, granulating, dragee-making levigating, emulsifying, encapsulating, entrapping or lyophilization processes. The compositions can be formulated in conventional manner using one or more physiologically acceptable carriers, diluents, excipients or auxiliaries that facilitate processing of the ALAC and/or ALFA compositions into preparations that can be used.

The compositions of the invention can take a form suitable for virtually any mode of administration, including, for example, oral, buccal, systemic, injection, transdermal, rectal, vaginal, etc., or a form suitable for administration by inhalation or insufflation.

Systemic formulations include those designed for administration by injection, e.g., subcutaneous, intravenous, intramuscular, intrathecal or intraperitoneal injection, as well as those designed for transdermal, transmucosal oral or pulmonary administration.

Useful injectable preparations include sterile suspensions, solutions or emulsions of the ALAC and/or ALFA compositions in aqueous or oily vehicles. The compositions can also contain formulating agents, such as suspending, stabilizing and/or dispersing agent. The formulations for injection can be presented in unit dosage form, e.g., in ampoules or in multi-dose containers, and can contain added preservatives.

Alternatively, the injectable formulation can be provided in powder form for reconstitution with a suitable vehicle, including but not limited to sterile pyrogen free water, buffer, dextrose solution, etc., before use. To this end, the ALAC and/or ALFA compositions can be dried by any art-known technique, such as lyophilization, and reconstituted prior to use.

For transmucosal administration, penetrants appropriate to the barrier to be permeated are used in the formulation. Such penetrants are known in the art.

For oral administration, the compositions of the invention can take the form of, for example, lozenges, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). The tablets can be coated by methods well known in the art with, for example, sugars, films or enteric coatings.

Liquid preparations for oral administration can take the form of, for example, elixirs, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol, or fractionated vegetable oils); and preservatives (e.g., methyl or propyl p hydroxybenzoates or sorbic acid). The preparations can also contain buffer salts, preservatives, flavoring, coloring and sweetening agents as appropriate.

Preparations for oral administration can be suitably formulated to give controlled release of the ALAC and/or ALFA composition as is well known.

For buccal administration, the compositions can take the form of tablets or lozenges formulated in conventional manner.

For rectal and vaginal routes of administration, the ALAC and/or ALFA compositions can be formulated as solutions (for retention enemas) suppositories or ointments containing conventional suppository bases such as cocoa butter or other glycerides.

For nasal administration or administration by inhalation or insufflation, the ALAC and/or ALFA compositions can be conveniently delivered in the form of an aerosol spray from pressurized packs or a nebulizer with the use of a suitable propellant, e.g., dichlorodifluoromethane, trichlorofluoromethane, dichlorotetrafluoroethane, fluorocarbons, carbon dioxide or other suitable gas. In the case of a pressurized aerosol, the dosage unit can be determined by providing a valve to deliver a metered amount. Capsules and cartridges for use in an inhaler or insufflator (for example capsules and cartridges comprised of gelatin) can be formulated containing a powder mix of the compound and a suitable powder base such as lactose or starch.

For prolonged delivery, the ALAC and/or ALFA compositions can be formulated as a depot preparation for administration by implantation or intramuscular injection. The ALAC and/or ALFA compositions can be formulated with suitable polymeric or hydrophobic materials (e.g., as an emulsion in an acceptable oil) or ion exchange resins, or as sparingly soluble derivatives, e.g., as a sparingly soluble salt. Alternatively, transdermal delivery systems manufactured as an adhesive disc or patch, which slowly releases the ALAC and/or ALFA compositions for percutaneous absorption, can be used. To this end, permeation enhancers can be used to facilitate transdermal penetration of the ALAC and/or ALFA compositions. Suitable transdermal patches are described in for example, U.S. Pat. Nos. 5,407,713; 5,352,456; 5,332,213; 5,336,168; 5,290,561; 5,254,346; 5,164,189; 5,163,899; 5,088,977; 5,087,240; 5,008,110; and 4,921,475.

Alternatively, other delivery systems can be employed. Liposomes and emulsions are well-known examples of delivery vehicles that can be used to deliver ALAC and/or ALFA compositions. Certain organic solvents such as dimethylsulfoxide (DMSO) can also be employed, although usually at the cost of greater toxicity.

The compositions can, if desired, be presented in a pack or dispenser device, which can contain one or more unit dosage forms containing the ALAC and/or ALFA compositions. The pack can, for example, comprise metal or plastic foil, such as a blister pack. The pack or dispenser device can be accompanied by instructions for administration.

Soft gel or soft gelatin capsules can be prepared, for example, without limitation, by dispersing the formulation in an appropriate vehicle (e.g., rice bran oil, and/or beeswax) to form a high viscosity mixture. This mixture is then encapsulated with a gelatin based film using technology and machinery known to those in the soft gel industry. The capsules so formed are then dried to constant weight. Typically, the weight of the capsule is between about 100 to about 2500 milligrams and in particular weigh between about 1500 and about 1900 milligrams, and more specifically can weigh between about 1500 and about 2000 milligrams.

For example, when preparing soft gelatin shells, the shell can include between about 20 to 70 percent gelatin, generally a plasticizer and about 5 to about 60% by weight sorbitol. The filling of the soft gelatin capsule is liquid (principally a carrier such as rice bran oil or wheat germ oil and/or beeswax if desired) and can include, apart from the ALAC and/or ALFA compositions, a hydrophilic matrix. The hydrophilic matrix, if present, is a polyethylene glycol having an average molecular weight of from about 200 to 1000. Further ingredients are optionally thickening agents and/or emulsifying agent(s). In one embodiment, the hydrophilic matrix includes polyethylene glycol having an average molecular weight of from about 200 to 1000, 5 to 15% glycerol, and 5 to 15% by weight of water. The polyethylene glycol can also be mixed with propylene glycol and/or propylene carbonate.

In another embodiment, the soft gel capsule is prepared from gelatin, glycerine, water and various additives. Typically, the percentage (by weight) of the gelatin is between about 30 and about 50 weight percent, in particular between about 35 and about weight percent and more specifically about 42 weight percent. The formulation includes between about 15 and about 25 weight percent glycerine, more particularly between about 17 and about 23 weight percent and more specifically about 20 weight percent glycerine.

The remaining portion of the capsule is typically water. The amount varies from between about 25 weigh percent and about 40 weight percent, more particularly between about 30 and about 35 weight percent, and more specifically about 35 weight percent. The remainder of the capsule can vary, generally, between about 2 and about 10 weight percent composed of a flavoring agent(s), sugar, coloring agent(s), etc. or combination thereof. After the capsule is processed, the water content of the final capsule is often between about 5 and about 10 weight percent, more particularly 7 and about 12 weight percent, and more specifically between about 9 and about 10 weight percent.

As for the manufacturing, it is contemplated that standard soft shell gelatin capsule manufacturing techniques can be used to prepare the soft-shell product. Examples of useful manufacturing techniques are the plate process, the rotary die process pioneered by R. P. Scherer, the process using the Norton capsule machine, and the Accogel machine and process developed by Lederle. Each of these processes are mature technologies and are all widely available to any one wishing to prepare soft gelatin capsules.

Emulsifying agents can be used to help solubilize the ingredients within the soft gelatin capsule. Specific examples of the surfactant, emulsifier, or effervescent agent include D-sorbitol, ethanol, carrageenan, carboxyvinyl polymer, carmellose sodium, guar gum, glycerol, glycerol fatty acid ester, cholesterol, white beeswax, dioctyl sodium sulfosuccinate, sucrose fatty acid ester, stearyl alcohol, stearic acid, polyoxyl 40 stearate, sorbitan sesquioleate, cetanol, gelatin, sorbitan fatty acid ester, talc, sorbitan trioleate, paraffin, potato starch, hydroxypropyl cellulose, propylene glycol, propylene glycol fatty acid ester, pectin, polyoxyethylene (105) polyoxypropylene (5) glycol, polyoxyethylene (160) polyoxypropylene (30) glycol, polyoxyethylene hydrogenated castor oil, polyoxyethylene hydrogenated castor oil 40, polyoxyethylene hydrogenated castor oil 60, polyoxyl 35 castor oil, polysorbate 20, polysorbate 60, polysorbate 80, macrogol 400, octyldodecyl myristate, methyl cellulose, sorbitan monooleate, glycerol monostearate, sorbitan monopalmitate, sorbitan monolaurate, lauryl dimethylamine oxide solution, sodium lauryl sulfate, lauromacrogol, dry sodium carbonate, tartaric acid, sodium hydroxide, purified soybean lecithin, soybean lecithin, potassium carbonate, sodium hydrogen carbonate, medium-chain triglyceride, citric anhydride, cotton seed oil-soybean oil mixture, and liquid paraffin.

The present invention also provides packaged formulations of the compositions of the invention and instructions for use of the product for appropriate condition(s). Typically, the packaged formulation, in whatever form, is administered to an individual in need thereof. Typically, the dosage requirement is between about 1 to about 4 dosages a day.

Although the present invention describes the preparation, use, manufacture and packaging of the compositions of the invention in soft gelatin capsules for treatment of various conditions, it should not be considered limited to only soft gelatin capsules. Ingestible compositions of the invention can be delivered in traditional tablets, pills, lozenges, elixirs, emulsions, hard capsules, liquids, suspensions, etc. as described above.

The ALAC and/or ALFA compositions of the invention, or compositions thereof, will generally be used in an amount effective to achieve the intended result, for example in an amount effective to treat or prevent the particular inflammatory related condition being treated. The composition can be administered therapeutically to achieve therapeutic benefit or prophylactically to achieve prophylactic benefit. By therapeutic benefit is meant eradication or amelioration of the underlying disorder being treated and/or eradication or amelioration of one or more of the symptoms associated with the underlying disorder such that the patient reports an improvement in feeling or condition, notwithstanding that the patient can still be afflicted with the underlying disorder. For example, administration of a composition of the invention to a patient suffering from pain provides therapeutic benefit not only when the underlying condition is eradicated or ameliorated, but also when the patient reports a decrease in the severity or duration of the physical discomfort associated with the pain.

For prophylactic administration, the composition can be administered to a patient at risk of developing one of the previously described conditions.

The amount of composition administered will depend upon a variety of factors, including, for example, the particular indication being treated, the mode of administration, whether the desired benefit is prophylactic or therapeutic, the severity of the indication being treated and the age and weight of the patient, etc. Determination of an effective dosage is well within the capabilities of those skilled in the art.

Total dosage amounts of an ALAC and/or ALFA composition will typically be in the range of from about 0.0001 or 0.001 or 0.01 mg/kg/day to about 100 mg/kg/day, but may be higher or lower, depending upon, among other factors, the activity of the components, its bioavailability, the mode of administration and various factors discussed above. Dosage amount and interval can be adjusted individually to provide plasma levels of the compound(s) which are sufficient to maintain therapeutic or prophylactic effect. For example, the compounds can be administered once per week, several times per week (e.g., every other day), once per day or multiple times per day, depending upon, among other things, the mode of administration, the specific indication being treated and the judgment of the prescribing physician. Skilled artisans will be able to optimize effective local dosages without undue experimentation.

The following paragraphs enumerated consequently from 1 through 63 provide for various aspects of the present invention. In one embodiment, in a first paragraph (1), the present invention provides a composition comprising a complex of oligomeric lipoic acid and a counterion(s).

2. The composition of paragraph 1, wherein the complex is a salt.

3. The composition of paragraph 1, wherein the complex is an association between the oligomeric lipoic acid and the counterion.

4. The composition of paragraph 3, wherein the association is chelation.

5. The composition of paragraph 1, wherein the counterion is an alkali metal, alkaline earth metal, ammonium ion, an amino acid, an alkylenediamine, a monosubstituted amine, a disubstituted amine, or a trisubstituted amine.

6. The composition of paragraph 1, wherein the counterion is an amino acid.

7. The composition of paragraph 6, wherein the amino acid is ornithine, arginine, lysine or mixtures thereof.

8. The composition of any of paragraphs 1 through 7, further comprising a salt of lipoic acid.

9. The composition of paragraph 8, wherein the salt of the lipoic acid comprises an amino acid.

10. The composition of paragraph 9, wherein the amino acid of the lipoic acid is ornithine, arginine, lysine or mixtures thereof.

11. The composition of any of paragraphs 1 through 10, wherein the composition is in solid form.

12. The composition of any of paragraphs 1 through 10, wherein the composition further comprises a liquid carrier.

13. A composition comprising:
an oligomeric lipoic acid complex comprising formula (I):

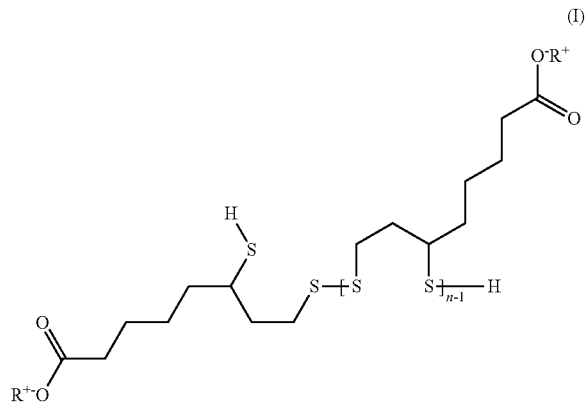

wherein each $R^+$ independently denote a counterion, and n is a value between about 2 to about 50.

14. The composition of paragraph 13, wherein the complex is a salt.

15. The composition of paragraph 13, wherein the complex is an association between the oligomeric lipoic acid and the counterion.

16. The composition of paragraph 15, wherein the association is chelation.

17. The composition of paragraph 13, wherein each $R^+$ independently is an alkali metal, alkaline earth metal, ammonium ion, an amino acid, an alkylenediamine, a monosubstituted amine, a disubstituted amine, or a trisubstituted amine.

18. The composition of paragraph 13, wherein each $R^+$ is an amino acid.

19. The composition of paragraph 18, wherein the amino acid is ornithine, arginine, lysine or mixtures thereof.

20. The composition of any of paragraphs 13 through 19, further comprising a salt of lipoic acid.

21. The composition of paragraph 20, wherein the salt of the lipoic acid comprises an amino acid.

22. The composition of paragraph 21, wherein the amino acid of the lipoic acid is ornithine, arginine, lysine or mixtures thereof.

23. The composition of any of paragraphs 13 through 22, wherein the composition is in solid form.

24. The composition of any of paragraphs 13 through 22, wherein the composition further comprises a liquid carrier.

25. A composition comprising: a complex of an oligomeric lipoic acid with a weight average (Mw) molecular weight of between about 412.6 and about 10268.5 daltons and a counterion.

26. The composition of paragraph 25, wherein the complex is a salt.

27. The composition of paragraph 25, wherein the complex is an association between the oligomeric lipoic acid and the counterion.

28. The composition of paragraph 27, wherein the association is chelation.

29. The composition of paragraph 25, wherein the counterion is an alkali metal, alkaline earth metal, ammonium ion, an amino acid, an alkylenediamine, a monosubstituted amine, a disubstituted amine, or a trisubstituted amine.

30. The composition of paragraph 25, wherein the counterion is an amino acid.

31. The composition of paragraph 30, wherein the amino acid is ornithine, arginine, lysine or mixtures thereof.

32. The composition of any of paragraphs 25 through 31, further comprising a salt of lipoic acid.

33. The composition of paragraph 32, wherein the salt of the lipoic acid comprises an amino acid.

34. The composition of paragraph 33, wherein the amino acid of the lipoic acid is ornithine, arginine, lysine or mixtures thereof.

35. The composition of any of paragraphs 25 through 34, wherein the composition is in solid form.

36. The composition of any of paragraphs 25 through 34, wherein the composition further comprises a liquid carrier.

37. An oligomeric lipoic acid complex prepared by the process of:
   a) reacting a base with lipoic acid in an aqueous solution;
   b) maintaining the solution at an elevated temperature for a period of between about 1 to about 5 hours; and
   c) precipitating a complex of the oligomeric lipoic acid and base counterion from the aqueous solution by addition of a non-solvent.

38. The oligomeric lipoic acid complex of the process of paragraph 37, further comprising the step of:
   d) collecting the precipitated complex.

39. The oligomeric lipoic acid complex of either of paragraphs 37 or 38, wherein the temperature of the reaction is between about 30° C. and about 50° C.

40. The oligomeric lipoic acid complex of any of paragraphs 37 through 39, wherein the solution was maintained at the elevated temperature for about 3 hours.

41. The oligomeric lipoic acid complex of any of paragraphs 37 through 40, wherein the non-solvent is an alcohol, a chlorinated hydrocarbon, an aliphatic ketone, an aliphatic ether, an alkyl hydrocarbon, an aromatic hydrocarbon or mixtures thereof.

42. The oligomeric lipoic acid complex of paragraph 41, wherein the non-solvent is one of acetonitrile, dichloromethane, acetone, 2-propanol, diethyl ether, hexane, octane, toluene, petroleum ether, tetrahydrofuran, octanol, benzene, dioxane or mixtures thereof.

43. The oligomeric lipoic acid complex of any of the paragraphs 37 through 42, wherein the base is an amino acid.

44. The oligomeric lipoic acid complex of paragraph 43, wherein the aqueous solution containing the amino acid is produced by adding NaOH to an aqueous solution containing the hydrochloride salt of the amino acid until a pH-value is obtained that has a value of from (I−0.4) to (I+0.4), wherein I is the iso-electric point of the amino acid.

45. The oligomeric lipoic acid complex of paragraph 44, wherein the pH-value is from I−0.1 to I.

46. The oligomeric lipoic acid complex of any of paragraphs 37 through 45, wherein the aqueous solution has a pH-value of from 9.5 to 10.0.

47. The oligomeric lipoic acid complex of any of paragraphs 43 through 46, wherein the amino acid is ornithine, arginine, lysine or mixtures thereof.

48. The oligomeric lipoic acid complex of any of paragraphs 37 through 47, further comprising an amino acid salt of lipoic acid.

49. The oligomeric lipoic acid complex of paragraph 48, where in the amino acid of the lipoic acid is ornithine, arginine, lysine or mixtures thereof.

50. The material of any of paragraphs 1 through 49, wherein the melting point is between about 165° C. and about 170° C.

51. The material of any of paragraphs 1 through 49, wherein the pH value is about 7.5 when 0.5 grams of the material is dissolved in 20 ml neutral water.

52. The material of any of paragraphs 1 through 49, wherein the lipoic acid and/or the oligomeric lipoic acid and/or formula (I) is the R enantiomer.

53. The material of any of paragraphs 1 through 49, wherein the lipoic acid and/or the oligomeric lipoic acid and/or formula (I) is the S enantiomer.

54. The material of any of paragraphs 1 through 49, wherein the lipoic acid and/or the oligomeric lipoic acid and/or formula (I) is racemic.

55. The material of any of paragraphs 6, 7, 9, 10, 18, 19, 20, 21, 30, 31, 32, 33 and 43 through 49, wherein the amino acid of the lipoic acid, and/or the oligomeric lipoic acid and/or formula (I) is the L form.

56. A pharmaceutical composition comprising any of paragraphs 1 through 11, 13 through 23, 25 through 35 and 37 through 55; and a pharmaceutically acceptable carrier.

57. A composition comprising:
an oligomeric lipoic acid comprising formula (Ia):

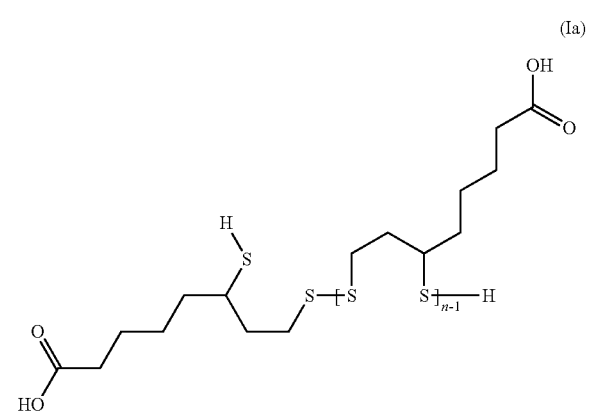

wherein n is a value between about 2 to about 50.

58. A pharmaceutical composition comprising the oligomeric lipoic acid of paragraph 57 and a pharmaceutically acceptable carrier.

59. A composition comprising a mixed oligomeric alpha lipoic acid complex comprising formula (II):

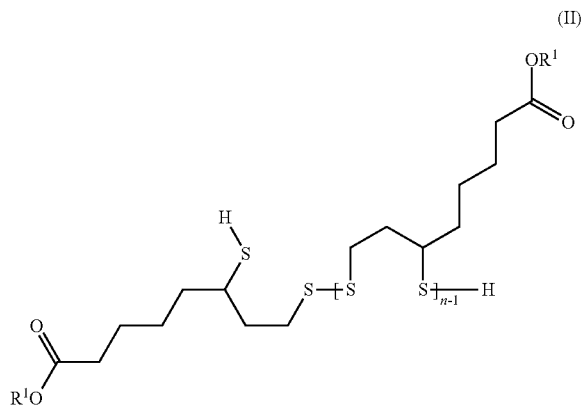

(II)

wherein n is a value between about 2 and about 50; and each $R^1$ independently is a hydrogen atom or counterion provided at least one $R^1$ is a counterion.

60. A pharmaceutical composition comprising the mixed oligomeric alpha lipoic acid complex of paragraph 59 and a pharmaceutically acceptable carrier.

61. A stabilized carotenoid or carotenoid derivative comprising a mixture of the oligomeric compositions of any of paragraphs 1 through 11, 13 through 23, 25 through 35, 37 through 55, 57 and 59 and a carotenoid or carotenoid derivative.

62. The stabilized carotenoid or carotenoid derivative of paragraph 61, wherein the oligomeric composition is coated onto the carotenoid or carotenoid derivative.

63. A method to stabilize a carotenoid or carotenoid derivative, comprising the steps:
contacting a carotenoid or carotenoid derivative with an oligomeric composition of any of paragraphs 1 through 11, 13 through 23, 25 through 35, 37 through 55, 57 and 59, such that the carotenoid or carotenoid derivative is stabilized.

The following examples are not to be meant as limiting but are presented to provide additional information and support for the invention.

In the following examples, the oligomeric compound of formula I with ornithine as the amino acid residue will be discussed in more detail. This compound will also be denoted with the term "LAORN".

Solubility of LAORN

LAORN has high solubility in water (>10% m/m; mass/mass), but does not dissolve well in organic solvents.

Demonstration of Ratio 1:1 Between the Lipoic Acid and Ornithine:

According to theoretical calculations, 1 molecule [Ornithine(+) Lipoic acid(−)] should contain 39% ornithine. Ornithine bears two atoms nitrogen. The calculation of the nitrogen content of 1 g of the above mentioned molecule yielded 83.4 mg/g. Determination of the nitrogen content according to Kjeldhal analysis provided 86.1 mg/g. That provides evidence for a 1:1 ratio in the oligomeric material.

Absence of the Thiolan Ring of Lipoic Acid

The thiolan-ring in lipoic acid has an absorption band around 320 nm which is also present in solutions of known salts of lipoic acid (such as K+, Na+). The new oligomeric material of LAORN lacks absorbance around 320 nm when measured immediately after dissolution in water, indicating that the thiolan ring is opened during the preparation of the new oligomeric material.

Liberation of α-Lipoic Acid

LAORN exhibits a pH-value of 7.5 when dissolved in water. The liberation of lipoic acid from LAORN after dissolution in water over time is depicted in FIG. 1.

Solubility of LAORN

The solubility of LAORN in various solvents was tested and compared with the solubility of α-lipoic acid. The results are shown in Table 1 below:

TABLE 1

Solubility of LAORN

| Solvent | LAORN | Lipoic Acid |
|---|---|---|
| Water | Soluble | Partly soluble |
| Acetylchloride | Partly soluble | Soluble |
| Acetonitrile | Insoluble | Soluble |
| Dichlormethane | Insoluble | Soluble |
| 2-Propanol | Insoluble | Soluble |
| Acetone | Insoluble | Soluble |
| Diethylether | Insoluble | Soluble |
| Hexane | Insoluble | Insoluble |
| Octane | Insoluble | Insoluble |
| Toluol | Insoluble | — |
| Petrolether | Insoluble | — |
| Tetrahydrofuran | Insoluble | — |
| Octanol | Insoluble | — |
| Benzene | Insoluble | — |
| Dioxane | Insoluble | — |

The solubility pattern suggests a salt. Most interestingly, LAORN, in contrast to α-lipoic acid, has a good water solubility (>10%).

Figure 2:
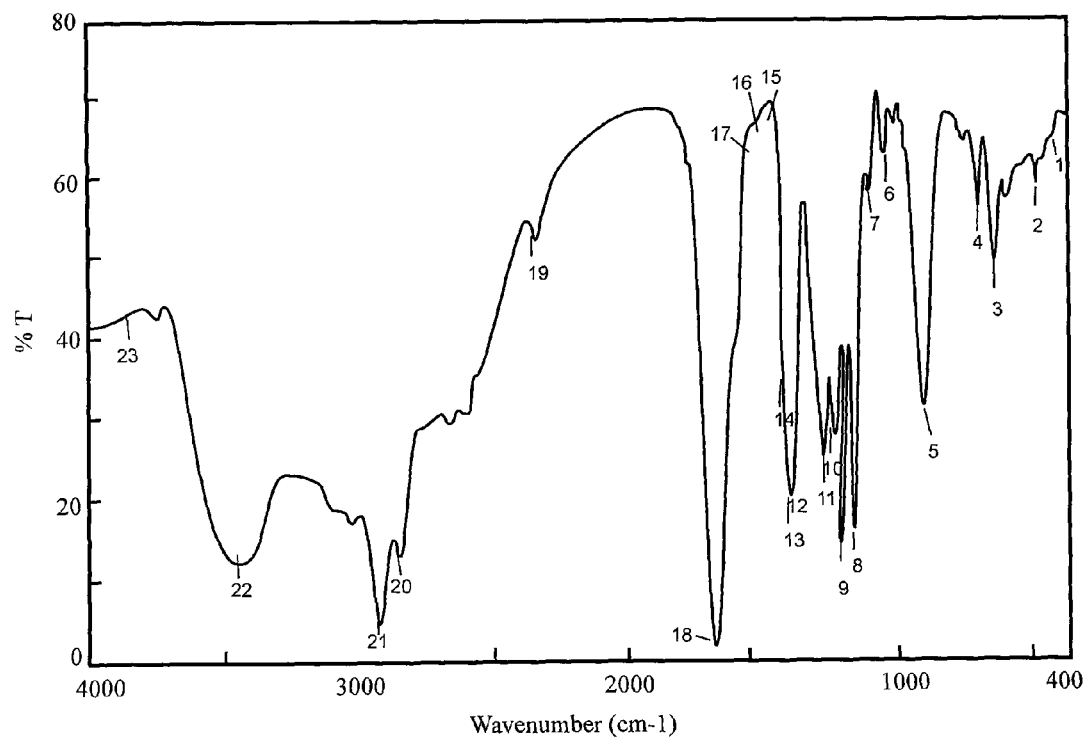
FIG. 2 shows the FT-IR spectra of α-lipoic acid.
Figure 3:
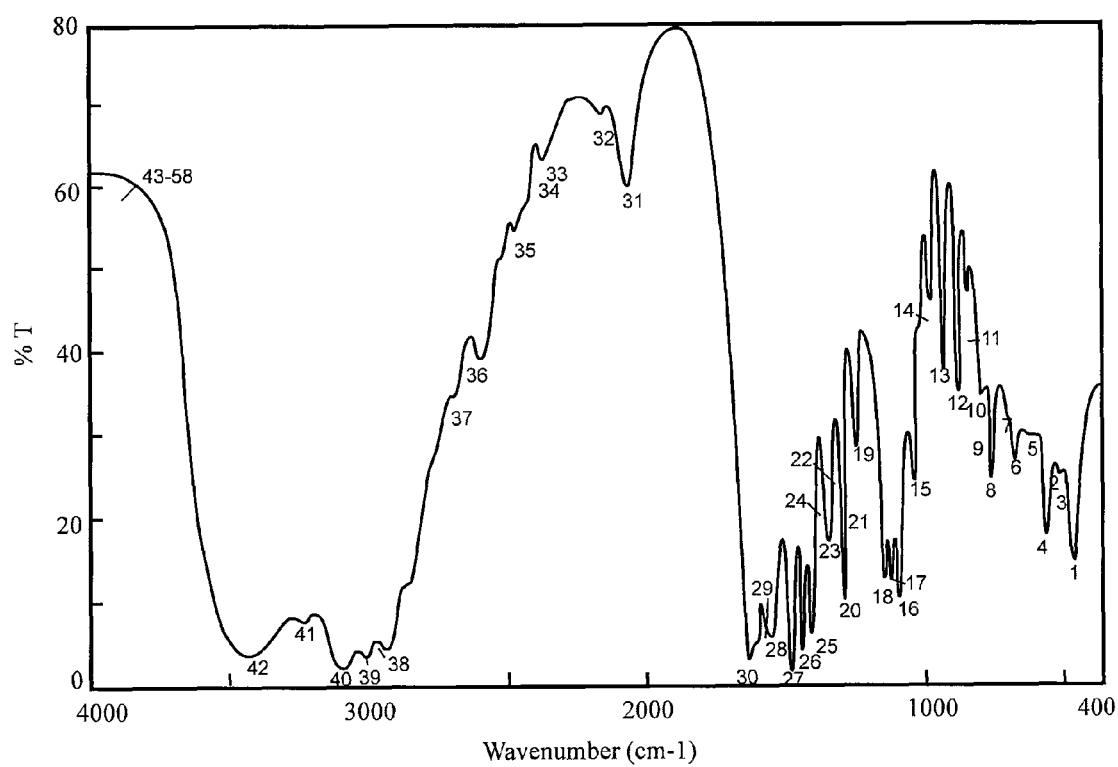
FIG. 3 shows the FT-IR spectra of LAORN.

FT-IR Spectroscopy:

FIGS. 2 and 3 show the FT-IR spectra of α-lipoic acid (FIG. 2) and LAORN (FIG. 3), respectively (solid KBr tablet).

The spectra indicate that α-lipoic acid is not present in LAORN. The typical FT-IR band of the disulfide bridge thiolan ring, present in lipoic acid (found at 1693 cm$^{-1}$) is missing in the LAORN material.

Figure 4:
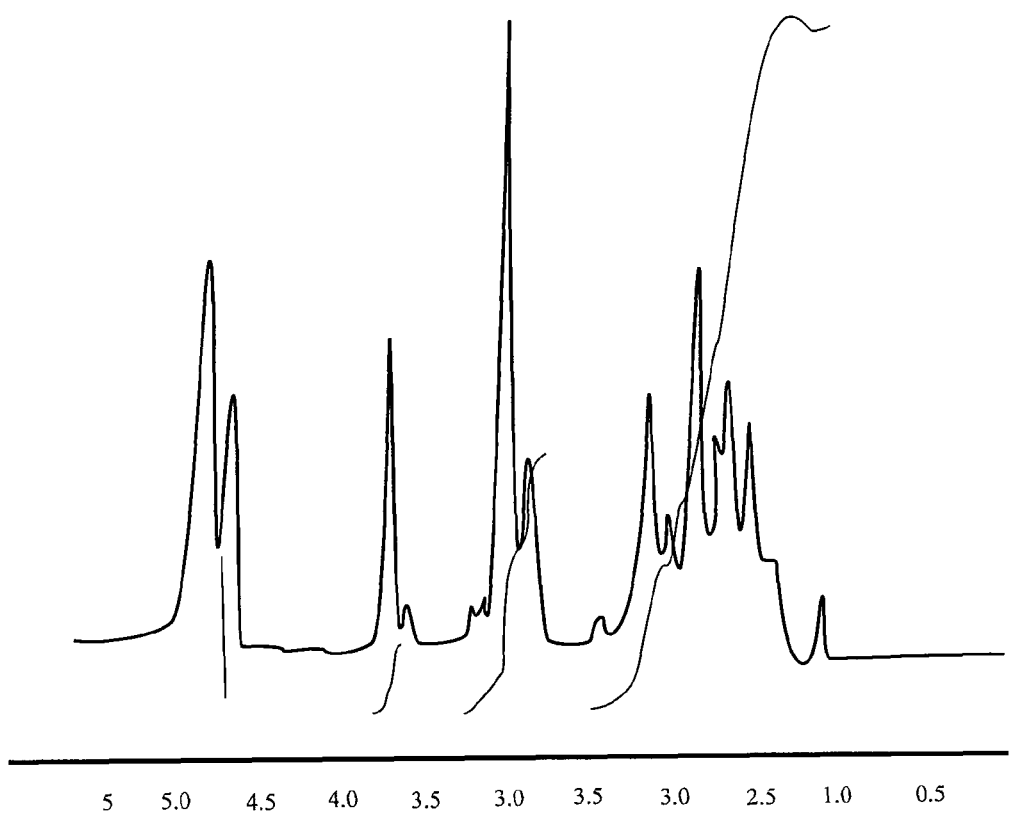
FIG. 4 provides the HNMR-spectrum (liquid) of LAORN.

NMR-Spectroscopy:

FIG. 4 provides the $^1$H NMR-spectrum (CDCl$_3$ liquid) of LAORN.

A band which refers to the amino acid-CH-proton in free state is visible as a triplet at 3 ppm. This provides evidence that the amino acid is not chemically bound to the lipoic acid residue (no amide bond).

Other Properties of LAORN

Upon addition of a small amount of acid (irrespective of the acid) to a concentrated solution of LAORN (>5% m/m) a rubbery mass forms immediately. Upon addition of a small amount of acid (irrespective of the acid) to a more diluted solution of LAORN (<1% m/m) a stable emulsion forms immediately.

As it is not soluble in diethylether, LAORN was dissolved in water and extracted with diethylether. Under these conditions the presence of polymers can be excluded as nothing was identified by thin layer chromatography. UV/VIS spectroscopy demonstrated an absence of any absorption at 320 nm for LAORN dissolved in water. Measurements were taken immediately upon dissolution of the LAORN material. This provides evidence to the absence of lipoic acid (thiolan-ring) in the LAORN material.

The product reacts with o-phthaldehyde positively as well as an artificial mixture of lipoic acid and ornithine. These observation provide the possibility to liberate of at least some free thiol groups and the presence of free amino acid functions.

LAORN shows a immediate reaction with $FeSO_4$ (brown $Fe(OH)_3$ appears).

Upon filtration a clear solution was obtained which does not build up any polymer upon addition of acid. This points to the fact that LAORN can be reduced and that thereby the polymerization process can be blocked.

Lipoic acid and dihydrolipoic acid are found at a ratio of 1:5 when LAORN is treated with mercaptoethanol. In contrast, the treatment of lipoic acid with mercaptoethanol yields a ratio of 1:0.6, respectively. This helps demonstrate the existence of an intermolecular —S—S— bond in LAORN.

Treatment of LAORN with $H_2O_2$ in neutral solution yields lipoic acid with no other peaks as identified by HPLC. Treatment of lipoic acid with $H_2O_2$ in neutral solution yields a significant distinct peak elution earlier than lipoic acid. It was confirmed that this peak is not influenced by the presence/absence of ornithine nor is it seen by treatment of ornithine alone. This helps to confirm that LAORN differs from lipoic acid.

Oxidation of lipoic acid to the corresponding thiosulfinate and thiosulfonate is described in the literature. Hence, again the presence of lipoic acid in LAORN can be excluded. Treatment of LAORN with $NaBH_4$ in alkaline solution yields almost immediately, 100% of theory of dihydrolipoic acid. In this respect lipoic acid reacts similar.

Antioxidative Capacity of LAORN

LAORN was tested for its total antioxidant capacity using a well established test assay. The test assay (Calbiochem, Cat. No. 615700) measures the ability of a given compound to suppress the formation of a radical. The oxidation of 2,2'-Atino-di-(3-ethylbenz-thiazoline sulphonate) (ABTS) with metmyoglobin yielding the ABTS+ radical was chosen. The radical formed can be monitored by analyzing absorbance at 600 nm. In situations where a radical scavenger is not introduced, the radical develops rapidly. Conversely, if a compound with radical scavenging properties is present, the development of the band at 600 nm is suppressed. The results are calibrated against a standard labeled with a 1.78 mmol antioxidant concentration.

Sample Preparation:

Pure α-lipoic acid and ornithine as well as (LAORN) were dissolved in water and adjusted to pH=7.5 with NaOH. The following concentrations were tested:

6.1 mg α-lipoic acid/10 mL
3.9 mg ornithine/10 mL
6.1 mg α-lipoic acid plus 3.9 mg ornithine/10 mL
10 mg LAORN/10 mL.

The concentrations were chosen based on the molar ratio of 1:1 for α-lipoic acid and ornithine. All 4 samples contained therefore 3 mmol of the corresponding compounds. In a test setting 2.5, 5 and 10 mg LAORN/10 mL (corresponding to 0.75, 1.5 and 3 mmol) were tested for the determination of the dose proportional response. Each sample was tested 3 times and the results provided are mean values. The precision of the 3 determinations was better than 3%.

Results

Figure 5:
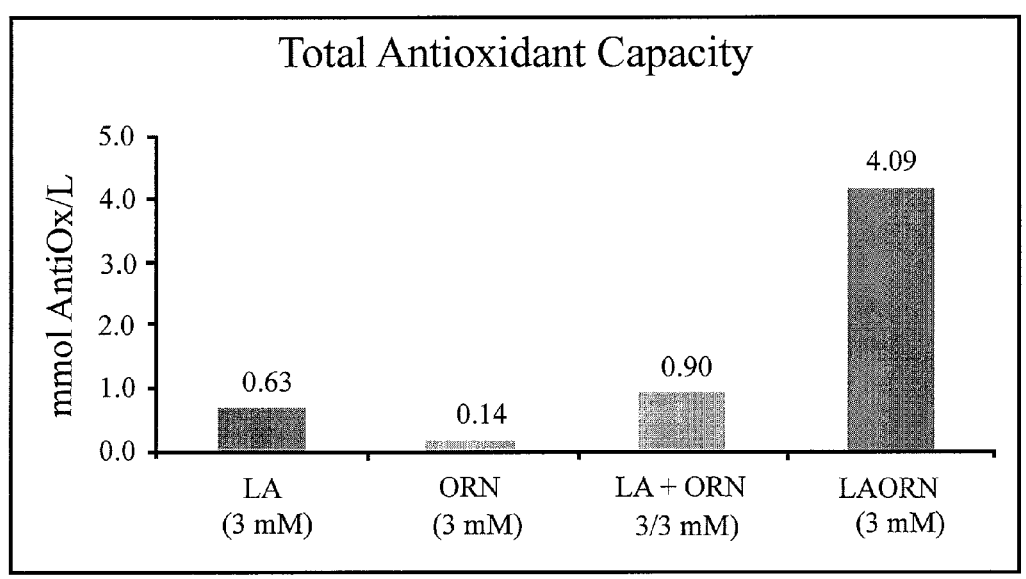
FIG. 5 shows the total antioxidant capacity in mmol/L for the samples containing 3 mmol corresponding compound/L.

FIG. 5 shows the total antioxidant capacity in mmol/L for the samples containing 3 mmol corresponding compound/L.

As is apparent from FIG. 5, LAORN acts synergistically when compared to pure lipoic acid, ornithine and an equimolar mixture of lipoic acid and ornithine.

LAORN is about 7 times more effective than lipoic acid and about 4.5 times more effective than a mixture of lipoic acid and ornithine.

Figure 6:
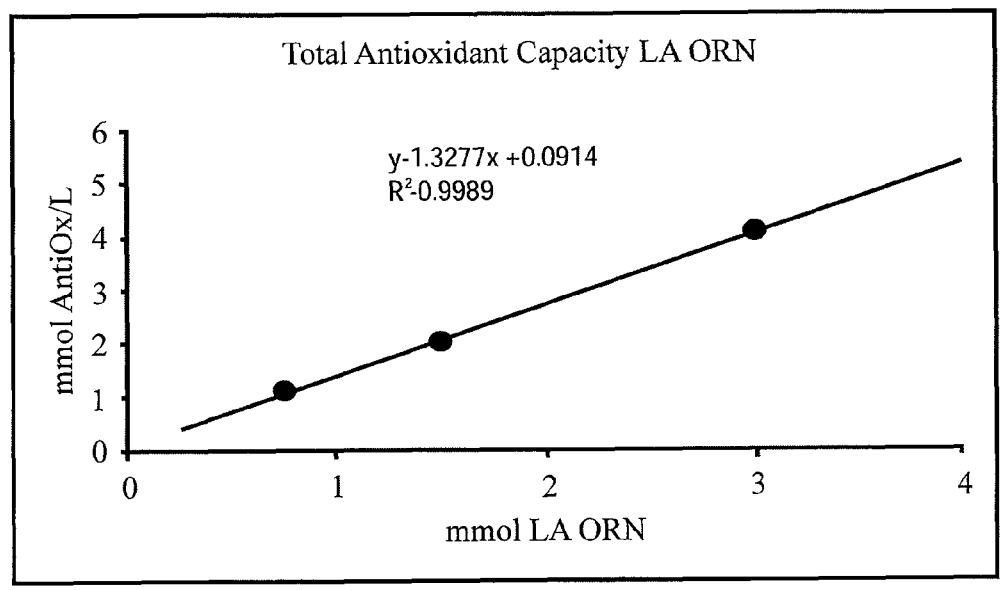
FIG. 6 shows the results for different concentrations of LAORN.

FIG. 6 shows the results for different concentrations of LAORN.

A linear dose-proportional increase of the total antioxidant capacity of LAORN was observed.

Inhibition of the Autooxidation of Linoleic Acid

This assay is based on the inhibition of accelerated autooxidation of linoleic acid determined at 50° C. Results are expressed as relative induction of the autooxidation when compared to negative control (no inhibition).

As a positive control (full inhibition) 10 mM butyl-hydroxytoluene (BHT)/L was introduced. Each sample was prepared in 3 replicates.

Figure 7:
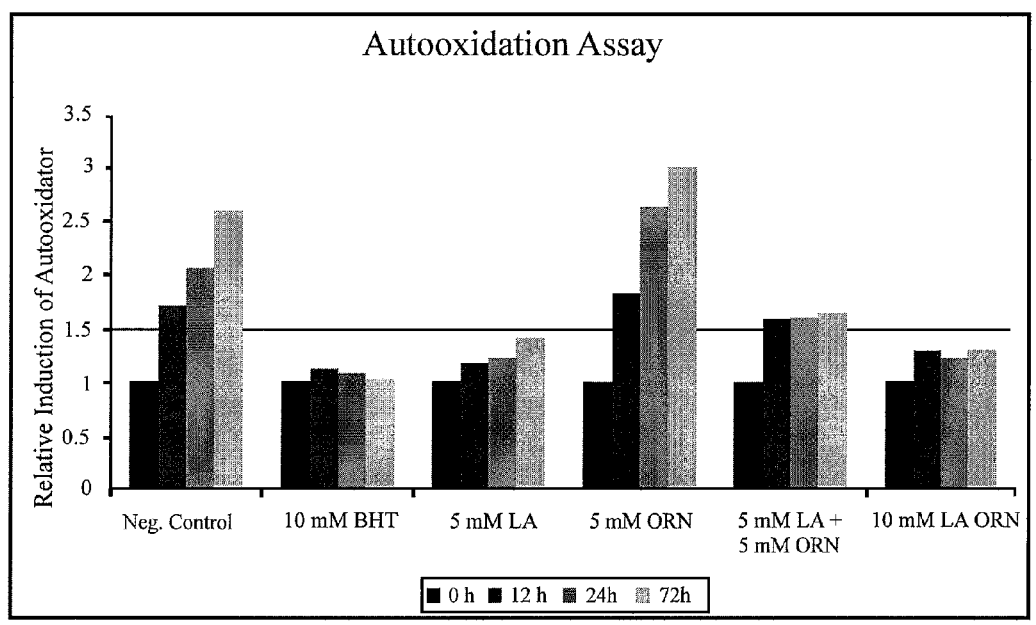
FIG. 7 shows the various time course of relative induction of auto-oxidation.

FIG. 7 shows the time course of induction obtained for
5 mM lipoic acid ("LA")/L
5 mM ornithine ("ORN")/L
5 mM lipoic acid/L+5 mM ornithine/L and
10 mM LAORN.

Additionally, the graph shows a threshold value at 1.5 indicating the induction period (values below indicate protection; values above indicate no more protection).

The positive control was shown to inhibit the autooxidation of linoleic acid for 72 hours at 50° C. Likewise, 5 mM LA/L yielded full protection over the period tested. As expected, the negative control yields considerable autooxidation after 12 hours of incubation.

After 12 hours of incubation the results obtained for 5 mM ORN/L indicate strongly that ornithine had no protective effect on the autooxidation of linoleic acid.

A mixture of 5 mM LA/L and 5 mM ORN/L was found to be borderline in its protective behavior whereas 10 mM LAORN/L was found to yield full protection.

Figure 8:
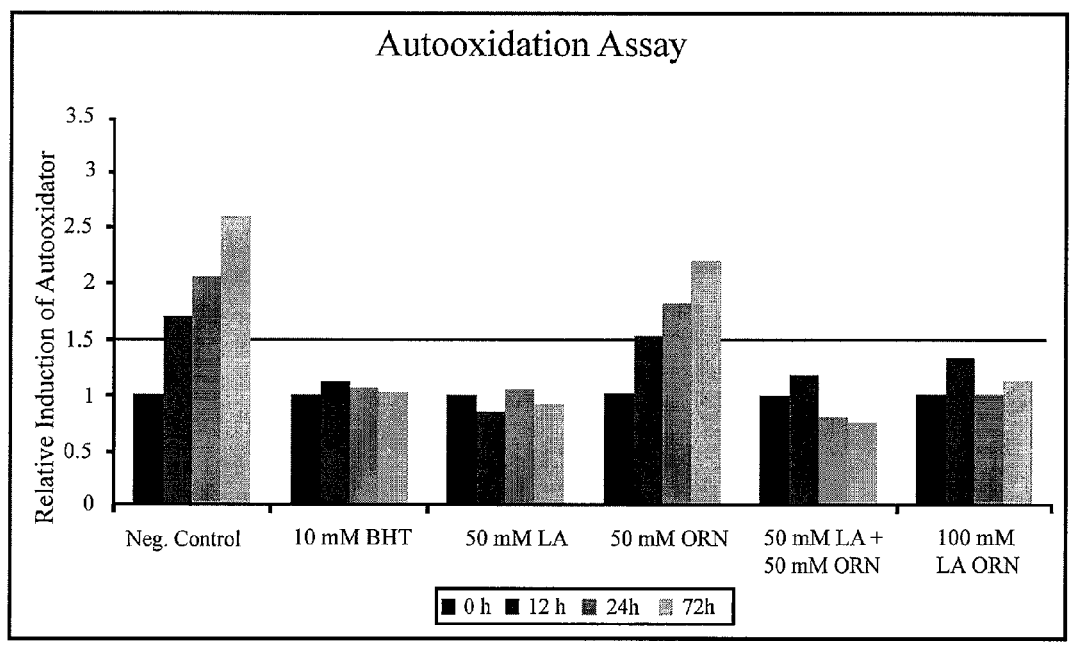
FIG. 8 shows the various time course of relative induction of auto-oxidation.

FIG. 8 shows the time course of induction obtained for 50 mM LA/L, 50 mM ORN/L, 50 mM LA/L+50 mM ORN/L and 100 mM LAORN/L.

Additionally, the graph shows a threshold value at 1.5 indicating the induction period (values below indicate protection; values above indicate no more protection).

The positive control was shown to inhibit the autooxidation of linoleic acid for 72 hours at 50° C. Likewise, 50 mM LA/L yielded full protection over the period tested. As expected, the negative control yields considerable autooxidation after 12 hours of incubation.

After 24 hours of incubation the results obtained for 50 mM ORN/L indicate strongly that ornithine had no protective effect on the autooxidation of linoleic acid.

A mixture of 50 mM LA/L and 50 mM ORN/L and 100 mM LAORN/L were found to yield full protection.

Method

Control: $H_2O$ (negative)

Butyl-hydroxytoluene (positive) 10, 50 and 100 mg/10 mL ($H_2O$, pH=8.0)

Samples: a) LA 0.1, 0.61, 1, 5, 6.1 and 10 mg/mL ($H_2O$, pH=8.0)
b) ORN 0.1, 0.39, 1, 3.9, 5 and 10 mg/mL ($H_2O$, pH=8.0)
c) LA+ORN 0.1, 1, 5 and 10 mg/l mL ($H_2O$, pH=8.0) at each level a ratio of 61/39.
d) LAORN 0.1, 1, 5 and 10 mg/10 mL ($H_2O$, pH=8.0)

Reagents: 25 mL 0.1 M Na-Phosphate buffer, pH=7.0
350 mg Linoleic acid/25 mL ethanol (95%)
Ethanol 75%
3.5% (mg/ml) hydrochloric acid
1.5 g Ammoniumthiocyanate/5 mL $H_2O$
25.0 mg Iron-II-Chloride/10 mL 3.5% HCl Sample incubation:

0.25 mL of each sample+0.5 mL buffer+0.5 mL Linoleic acid solution were transferred into a 2 mL plastic vial with tight screw caps. Each sample was prepared in 3 replicates.

Samples were incubated with light protection at 50° C.

Autooxidation was tested at time point zero and after 12, 24 and 72 hours.

Test assay: Mix 25 μL incubated sample with 1.20 mL Ethanol 75% and 25 μL Ammoniumthiocyanate and 25 μL Iron-II Chloride Read absorption at 500 nm after 3 minutes mixing.

Results for the assay of the reducing power:

The assay is based on the reduction of Iron-III to Iron-II. Results are expressed as % reduction when compared to the control which reduced all Iron-III at a concentration of 5 mg/mL.

Figure 9:
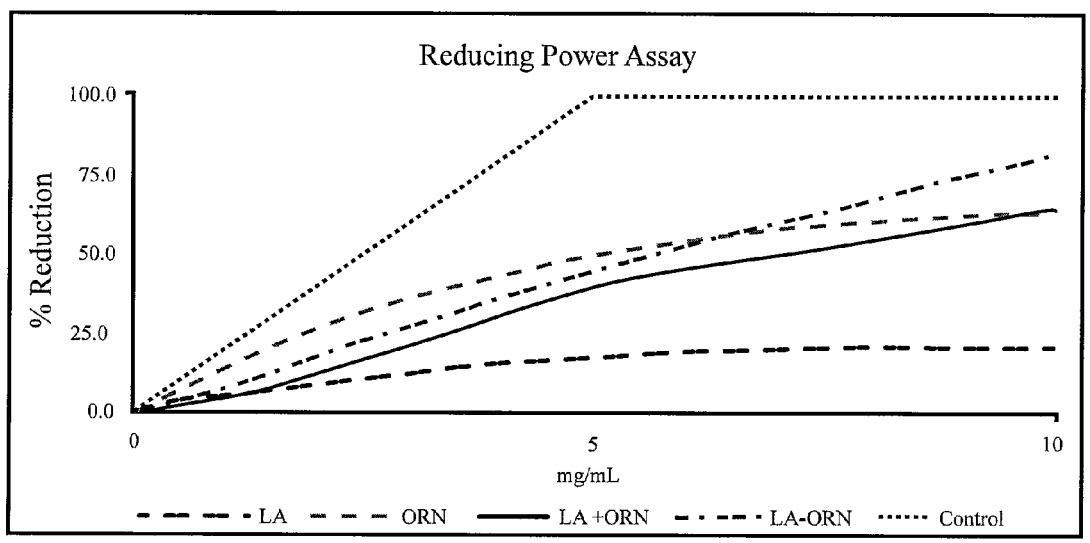
FIG. 9 provides the results of the reducing power assay.

FIG. 9 provides the results of the reducing power assay.

Furthermore, Table 2 summarizes the results of the reducing power assay.

TABLE 2

| Conc. mg/mL | % Reduction compared to Control | | | | |
|---|---|---|---|---|---|
| | LA | LA + ORN | ORN | LAORN | Control |
| 0 | 0.0 | 0.0 | 0.0 | 0.0 | 0.0 |
| 1 | 7.2 | 5.8 | 19.9 | 12.0 | 22.7 |
| 5 | 22.2 | 41.5 | 53.3 | 47.4 | 100.0 |
| 10 | 24.7 | 64.2 | 64.5 | 81.9 | 100.0 |

Legend:
LA . . . Lipoic Acid,
ORN . . . Ornithine,
LA + ORN . . . equimolar mixture of LA and ORN, LAORN,
Control is $NaBH_4$.

Figure 10:
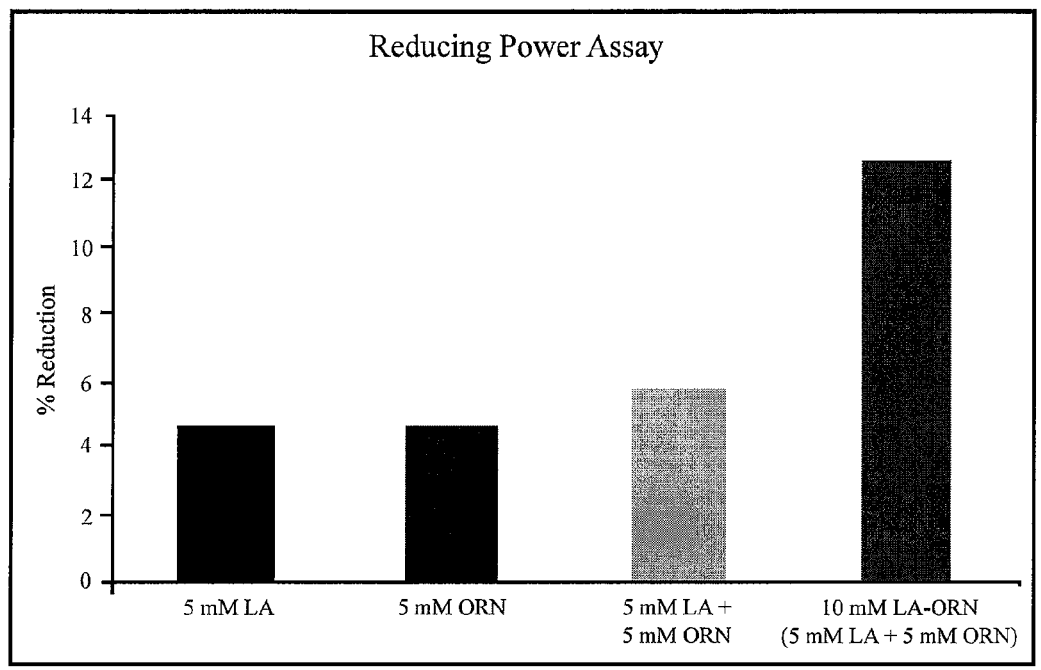
FIG. 10 shows LAORN had a strong synergistic effect when compared to a simple mixture of LA and ORN.

In a further test, LA and ORN were analyzed separately at a concentration of 5 mM/L. Furthermore, a mixture of LA and ORN consisting of 5 mM LA/L and 5 mM ORN/L was tested. Finally, 10 mM LAORN/L was tested. As seen in FIG. 10, LAORN had a strong synergistic effect when compared to a simple mixture of LA and ORN.

Methods of Preparation:

EXAMPLE 1

16.8 g (0.1 mol) L-Ornithine-HCl-Salt was dissolved in 160 ml water. The solution was stirred until the L-Ornithine HCl-salt was totally dissolved. The pH-value of the solution was 4.6.

4 g (0.1 mol) NaOH were added to the above solution. The mixture was stirred until the NaOH was totally dissolved. The pH value of the solution was 9.6.

20.6 gram α-lipoic acid (0.1 mol) were slowly added into the above solution. The mixture was stirred until the α-lipoic acid was totally dissolved.

The mixture was kept at 40° C. for three five hours. At the end of this time period, the solution was concentrated under reduced pressure (50° C., vacuum at 0.09 mpa) until 50% of the water was removed. By doing so, all possible organic solvents in raw material would be evaporated. This took around 5 hours. The volume of remaining solution was around 100 ml, the pH-value was 7.5.

The concentrated solution was poured into 1250 ml ethanol (95%). The resulting solution was stirred and a white precipitate was formed. The water content of solution was controlled below 11%. The solution was filtered to obtain the precipitate. The mother liquid can be used again for recovering ethanol and to obtain further product.

The precipitate was dried at about 35° C. for 6 hours. 27 grams of the product LAORN, according to the invention are obtained.

Appearance: slightly yellowish powder
Melting Point: 165~170° C.
PH value: 7.56 (0.5 gram dissolved in 20 ml water)
Influence of reaction time, concentration of reagents and temperature Several tests were conducted with regard to the influence of reaction time, concentration of reagents and temperature. The degree of oligomerization of the α-lipoic acid starting material was measured in terms of the specific rotation of the reaction solution. By oligomerization of the lipoic acid, the S—S-bond of the lipoic acid is broken, which amounts to a change in the specific rotation. The lower the specific rotation is, the higher is the formation of the oligomerized compound according to the invention.

Determination of Optical Rotation (By polarimeter, type: WZZ-3, producer: Shanghai precision & Scientific Instrument Co, Ltd)

0.2544 g of LAORN (Example 1 sample) was placed into a 25 ml volumetric flask and diluted with deionized water until the total volume equaled 25 mL providing a resultant concentration of 0.1076 g/100 ml. Deionized water was used as a control and the optical rotation was determined of the deionized water. An aqueous sample of the LAORN was then tested and found to have a specific optical rotation of sample is 5.45°.

Figure 11:
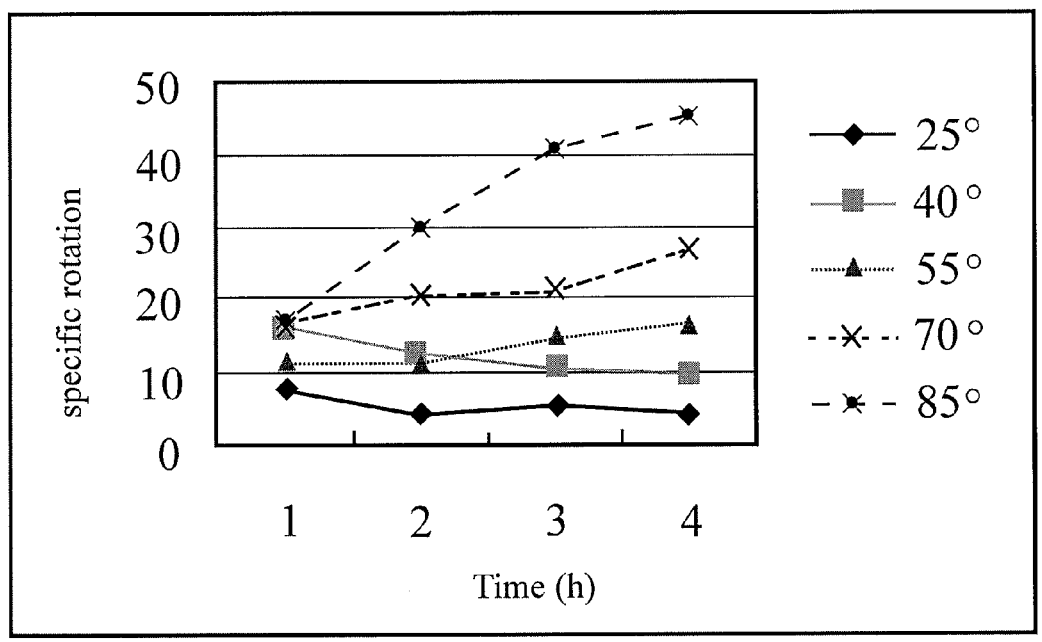
FIG. 11 shows the influence of reaction time and temperature on the LAORN formation.

FIG. 11 shows the influence of reaction time and temperature on the LAORN formation.

It can be seen that LAORN formation is higher at lower temperatures. However the viscosity of the solution can limit the minimum temperature to some extent. Therefore, temperatures of from 30° C. to 50° C. were found to be optimal.

Furthermore, it appears from FIG. 11 that there is no significant production of LAORN after 3 hours of reaction time under the given reaction conditions.

Figure 12:
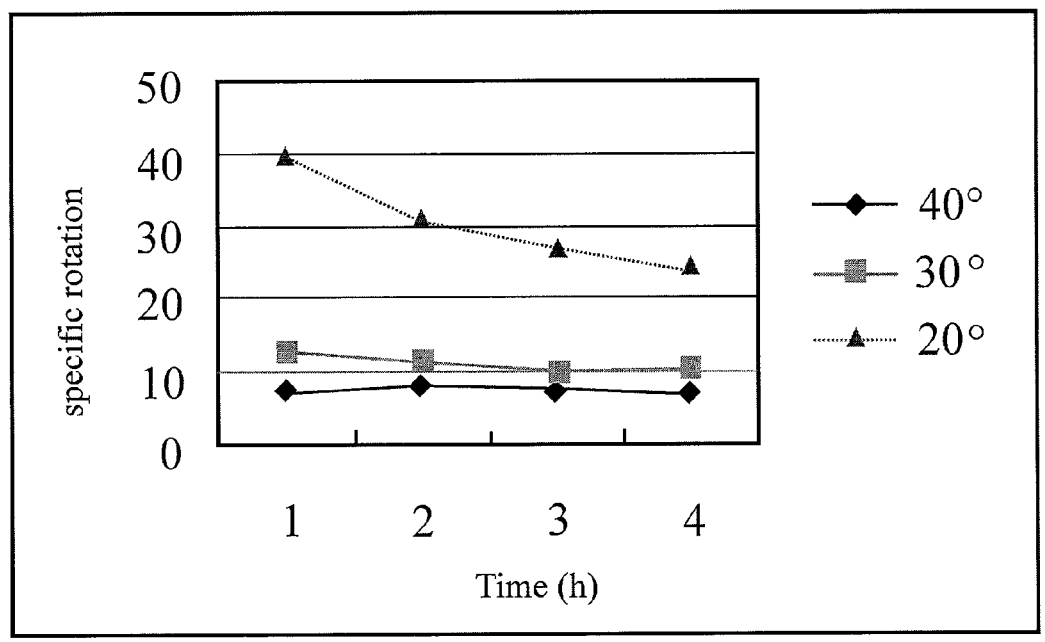
FIG. 12 shows the effect of the concentration of two reagents [LA+ORN] (the concentration is the sum of each reagent's concentration, and the molar ratio of them is 1:1) on LAORN formation.

FIG. 12 shows the effect of the concentration of two reagents [LA+ORN] (the concentration is the sum of each reagent's concentration, and the molar ratio of them is 1:1) on LAORN formation. It was found that the higher the concentration is, the higher is LAORN formation. However, again, high viscosity of the solution imposes a limit to a maximum concentration. Therefore, the concentration is preferably from 25% to 35% (w/v).

Determination of average polymerization degree of lipoic acid in LAORN by Iodimetry method Test Principle Iodine can oxidize sulfhydryl (—SH) group quantitatively. Superfluous iodine is titrated by $Na_2S_2O_3$ standard solution. By measurement of the consumption of iodine, the content of —SH group in system can be determined, and then the average degree of polymerization can be calculated.

Reagents

All analytical reagents were of analytical purity. Deionized water was used.

Hydrochloric acid (HCl) solution: prepared with 36% concentrated hydrochloric acid and deionized water (v/v, 1/1).

Potassium dichromate $(K_2Cr_2O_7)$ standard solution: $K_2Cr_2O_7$ (dried at 105° C., 2 h) 4903.0 mg was diluted to 1000 ml in a volumetric flask with deionized water.

Starch-iodide indicator: 1 g of soluble starch was added to enough water to form a paste. The paste was then diluted to 100 ml with additional water.

$Na_2S_2O_3$ standard solution
Preparation 24.5 g $Na_2S_2O_3.5H_2O$ and 0.2 g $Na_2CO_3$ were dissolved with water, transferred to 1000 ml brown glass volumetric flask and diluted to volume with additional water. The resulting solution was mixed well.

Titration
Reaction Equation $$3Na_2S_2O_3+K_2Cr_2O_7+6HCl \rightarrow 2Cr(OH)SO_4+4NaCl+3S+Na_2SO_4+2KCl$$

1 g potassium iodide (KI) and 50 mL water were added to 250 mL iodine numoe flask, to which was added 15.00 mL $K_2Cr_2O_7$ standard solution and 5 ml HCl (v/v, 1/1) to the flask. The flask was closed, the solution was mixed well and allowed to stand still for 5 minutes in dark. Upon titration of the solution to a light yellow with $Na_2S_2O_3$ solution, 0.5 ml starch-iodide indicator was added. The titration was stopped as the blue color disappeared. Record standard solution quantity, and titrate blank solution at the same time.

Calculation of $Na_2S_2O_3$ standard solution concentration as following:

$$c = \frac{a}{294.18} \cdot \frac{15.00}{(V_1 - V_2)} \cdot \frac{3}{1000}$$

a weight of $K_2Cr_2O_7$, mg
$V_1$ volume of $Na_2S_2O_3$ solution used to titrate $K_2Cr_2O_7$ solution, ml
$V_2$ volume of $Na_2S_2O_3$ solution used to titrate blank solution, ml Dilution
The $Na_2S_2O_3$ solution was diluted to 1/10 the original concentration before using. An Iodine standard solution was prepared by combining 1.27 g iodine and 4.0 g KI in a 1000 ml volumetric flask and diluting to 1000 ml with water.

Test Methods
About 20 mg of sample were weighed accurately to which were added 5 ml DMF, 5 ml HCl solution (1/1, v/v), and 10.00 ml iodine standard solution. The sample was airproofed and place in the dark for 10 min, and then titrated with the $Na_2S_2O_3$ solution. When the solution turned to light yellow in color, 0.2 ml starch-iodide indicator was added. The titration was continued until the resultant blue color disappeared. This volume was noted as $V_4$.

For the blank titration, one blank sample is prepared with 10.00 ml iodine standard solution, 5 ml HCl solution (1/1, v/v). The titration is performed as outlined above and the volume was noted as $V_3$.

Reaction Equation $$2Na_2S_2O_3+I_2 \rightarrow 2NaI+Na_2S_4O_6$$

$$d = c \cdot (V_3 - V_4) \cdot \frac{1}{10}$$

c=concentration of $Na_2S_2O_3$ solution, mol. $L^{-1}$
$V_3$ volume of $Na_2S_2O_3$ solution that was used to titrate blank solution, ml
$V_4$ volume of $Na_2S_2O_3$ solution that was used to titrate sample, ml Calculation of average polymerization degree $\bar{n}$ as following:

$$\bar{n} = \frac{M}{338.51} \cdot \frac{1}{d}$$

M weight of LAORN, mg

Correction of Free Lipoic Acid
Since there is some free (un-polymerized) lipoic acid in the sample, this portion of the lipoic acid needed to be accounted for in the calculation. This correction is provided as follows: 2, 5, 7, 10, 15, 20 mg lipoic acid standard were measured, metered volume to 10 ml and analyzed with the HPLC, UV detector at 220 wavelength.

Figure 20:
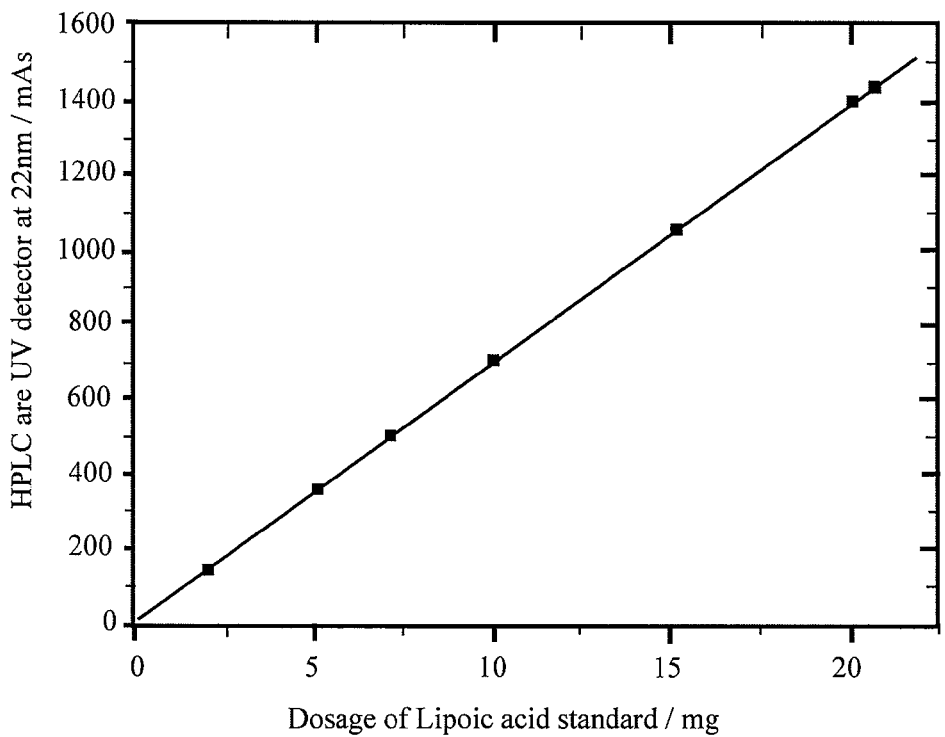
FIG. 20 depicts a titration curve for lipoic acid.

A calibrate curve was prepared as follows (See FIG. 20):

| Dosage of Lipoic Acid/mg | HPLC Peak Area/mAs |
|---|---|
| 2.01 | 143.2 |
| 5.14 | 356.8 |
| 7.11 | 497.5 |
| 10.02 | 701.0 |
| 15.20 | 1051.4 |
| 20.14 | 1401.8 |

Correction of Iodine Consumed by Lipoic Acid
In the titration process, lipoic acid will slowly open the dithiane ring and this will also consume some iodine. To accurately determine the average degree of polymerization, this also needed to be accounted for in measuring iodine uptake.

Figure 21:
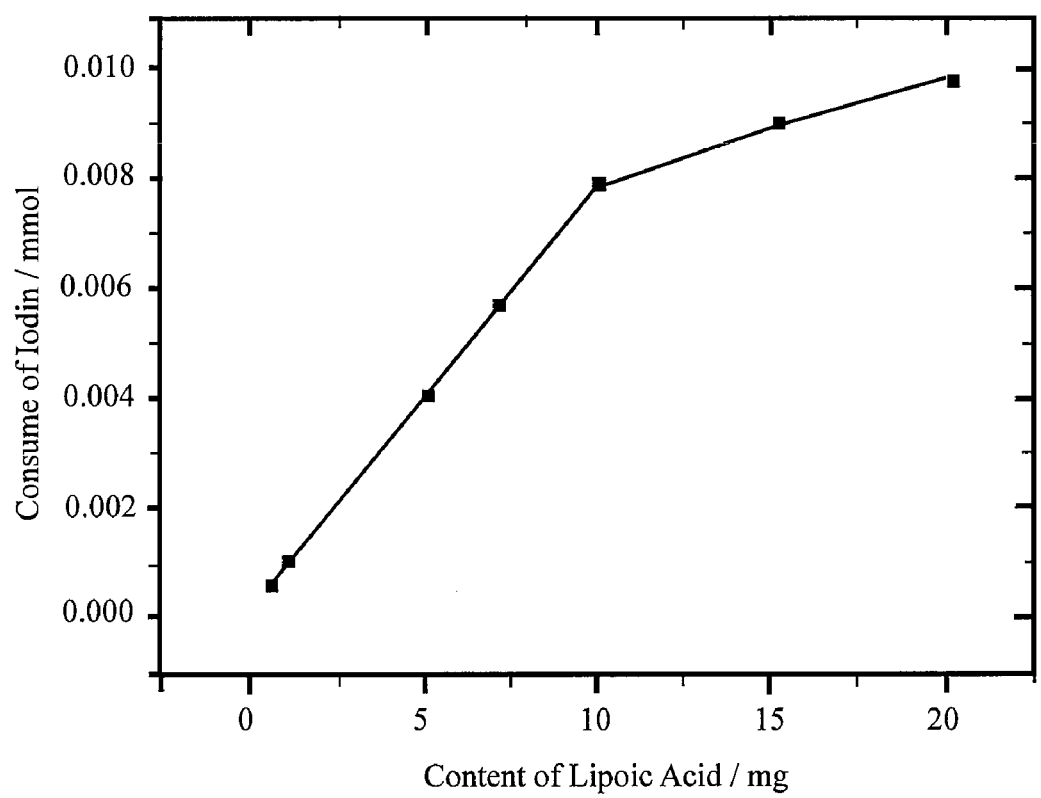
FIG. 21 depicts a titration curve for lipoic acid.

0.5, 1, 5, 7, 10, 15, 20 mg lipoic acid standards were weighed and measured with the method described above to calculate the iodine consumption of each sample. The results are provided below an in FIG. 21:

| Dosage of lipoic acid/mg | Iodine consumption/mmol |
|---|---|
| 0.53 | 0.00057 |
| 1.04 | 0.00105 |
| 5.09 | 0.00412 |
| 7.11 | 0.00573 |
| 10.02 | 0.00794 |
| 15.20 | 0.00905 |
| 20.14 | 0.00981 |

Test Example
Standard Solution Preparation
Potassium dichromate ($K_2Cr_2O_7$) standard solution was prepared by adding $K_2Cr_2O_7$ reagent (dried at 105° C., 2 h) 5373.4 mg to a 1000 ml volumetric flask and diluted to volume with water.

Iodine standard solution was prepared by combining 1.274 g iodine and 4.0 g KI in a 1000 ml volumetric flask and dilute to volume with water. The solution was mixed well.

$Na_2S_2O_3$ standard solution was prepared by combining 24.5 g $Na_2S_2O_3 \cdot 5H_2O$ and 0.2 g $Na_2CO_3$ with water, transferred to 1000 ml brown glass volumetric flask and diluted to volume with water. The solution was mixed well. Through titration, $K_2Cr_2O_7$ standard solution wastage is 16.8 ml. Thus the concentration of $Na_2S_2O_3$ standard solution was determined to be 0.0489 mol/$L^{-1}$.

Sample Test
According to above test method, 20.64 mg of LAORN (from Example 1) consumed 7.3 ml of $Na_2S_2O_3$ solution, thus iodine wastage is 0.0145 mmol. The average polymerization degree $\bar{n}$ was therefore, 4.21.

Result Correction
Free Lipoic Acid Correction
Sample weight was 100.08 mg. HPLC provided that the peak area of lipoic acid was 297.9 mAs, therefore it was determined that the sample contained about 4.3% free lipoic acid. This amount was deducted from the sample weight M.

Correction of Iodine Consumption

Since the sample for titration was 20.64 mg, the free lipoic acid was 0.888 mg, and the correction of iodine consumption was 0.0009 mmol. This was deducted from the iodine consumption d.

After inclusion of the two corrected values, the corrected average polymerization degree was determined to be about 4.17.

Example (Sodium-Lipoic Acid)

0.1 mol NaOH was dissolved in 160 ml water to which 20.6 g α-lipoic acid (0.1 mol) was slowly added with stirring. After the α-lipoic acid was totally dissolved, the mixture was maintained at 40° C. for three hours. The solution was concentrated under reduced pressure (vacuum at −0.09 mpa) at 50° C. until approximately 50% of the water was removed.

The concentrated solution was poured into 1250 ml ethanol (95%). The resulting solution was stirred with formation of a white precipitate. The precipitate was collected and then dried at about 35° C. for 6 hours. The resulting precipitate was determined to be sodium-lipoic acid salt with the average polymerization degree of about 14 (determined by the above test method).

Example (Potassium-Lipoic Acid)

0.1 mol KOH was dissolved in 160 ml water to which 20.6 g α-lipoic acid (0.1 mol) was slowly added with stirring. After the α-lipoic acid was totally dissolved, the mixture was maintained at 50° C. for five hours. The solution was concentrated under reduced pressure (vacuum at −0.09 mpa) at 50° C. until approximately 50% of the water was removed.

The concentrated solution was spray dried to afford potassium-lipoic acid salt with the average polymerization degree of about 14 (determined by the above test method).

Example (Ammonium-Lipoic Acid)

0.1 mol aqueous ammonia was added into 160 ml water to which 20.6 g α-lipoic acid (0.1 mol) was slowly added with stirring. After the α-lipoic acid was totally dissolved, the mixture was maintained at 45° C. for five hours. The solution was concentrated under reduced pressure (vacuum at −0.09 mpa) at 50° C. until approximately 50% of the water was removed.

The concentrated solution was spray dry dried to afford potassium-lipoic acid salt as a powder with the average polymerization degree of about 11 (determined by the above test method).

Example (Ethylene Diamine-Lipoic Acid)

0.1 mol ethylene diamine was dissolved in 160 ml water to which 20.6 g α-lipoic acid (0.1 mol) was slowly added with stirring. After the α-lipoic acid was totally dissolved, the mixture was maintained at 40° C. for five hours. The solution was concentrated under reduced pressure (vacuum at −0.09 mpa) at 50° C. until approximately 50% of the water was removed.

The concentrated solution was poured into 1250 ml ethanol (95%). The resulting solution was stirred with formation of a white precipitate. The precipitate was collected and dried at about 35° C. for 6 hours. The resulting precipitate was determined to be sodium-lipoic acid salt with the average polymerization degree of about 8 (determined by the above test method).

Example (Diethylamine-Lipoic Acid)

0.1 mol diethylamine was added into 160 ml water to which 20.6 g α-lipoic acid (0.1 mol) was slowly added with stirring. After the α-lipoic acid was totally dissolved, the mixture was maintained at 45° C. for five hours. The mixture was concentrated under reduced pressure (vacuum at −0.09 mpa) at 50° C. until approximately 50% of the water was removed.

The concentrated solution was spray dried to afford potassium-lipoic acid salt as a powder with the average polymerization degree of about 8 (determined by the above test method).

Example (Calcium Salt)

To 7.4 g (0.1 mol) calcium hydroxide and 160 ml water was added 20.6 g (0.1 mol) lipoic acid. A light yellow precipitate appeared in the reaction mixture. The mixture was maintained at approximately 50° C. for about 4 hours. The mixture was concentrated under reduced pressure until approximately 50% of the water was removed. The precipitate was filtrated, washed with 50 ml water and then vacuum dried. The polymerization degree was about 4 (determined by the above test method).

Example (Quinoline-Lipoic Acid Salt)

To 12.9 g (0.1 mol) quinoline and 50 ml water was added 20.6 g (0.1 mol) lipoic acid. The reaction mixture was stirred for about 30 minutes followed by removal of water under vacuum at 50° C. over a period of approximately 2 hours. The resulting product was vacuum dried. The average polymerization degree was about 4 (determined by the above test method).

Example (Isoquinoline-Lipoic Acid Salt)

To 0.1 mol isoquinoline and 50 ml water was added 20.6 g (0.1 mol) lipoic acid. The mixture was stirred for about 30 minutes followed by removal of water under vacuum at 50° C. over a period of approximately 2 hours. The resulting product was vacuum dried. The average polymerization degree was about 4 (determined by the above test method).

CACO-2 Absorption Test of LAORN in Comparison to LA

Methods

Culturing of CaCo-2 Cells

CaCo-2 cells were cultured in Dulbeccos's Modified Eagle Medium containing 20% fetal bovine serum, 1, 2% nonessential amino acids, 0.83 mM L-glutamine, 1, 2% penicillin-streptomycin and 0,1% mercaptoethanol in an atmosphere of 5% CO2 and 95% air at 37° C.

Cells were grown in 75 cm$^2$ culture-flasks (T75) and sub-cultured after one week (every other day washed with PBS buffer, removed with trypsin and transferred to an new culture flask).

CaCo-2 Test

For experiments, cells were seeded in 6 well plates at a density of $3 \times 10^5$ cells per well and grown in an atmosphere of 5% $CO_2$ and 95% air at 37° C. 7 to 8 days until confluency was reached. The cells were washed with PBS buffer, incubated with 4 ml medium containing lipoic acid (1 mg/mL medium) or LAORN (1.45 mg/mL medium, equivalent to 1 mg LA) for 30 and 60 minutes.

After incubation, the cells were washed with PBS buffer and removed using 1 ml 0.1 PBS buffer. Cells were sonicated 3 times for 30 seconds, centrifuged for 10 min and the pellets were discarded. The supernatant was used as sample for further analysis.

For stability investigations, the incubation medium was incubated at 37° C. for 1 hour. Thereafter, the medium was centrifuged and used for further analysis.

Sample Preparations for Analysis a) Analysis of Free LA and DHLA

The samples taken were submitted to HPLC analysis with further sample preparation described below.

b) Reduction of LA or LAORN to DHLA 1 ml sample (medium or cells) were mixed with 1 ml NaBH$_4$ (200 mg/100 mL 0.1 N NaOH) and incubated for 10 min at 60° C. Thereafter 2 ml 2 M HCl were added and the sample was extracted with 3×2 ml diethylether. The combined organic phases were evaporated and reconstituted with 1 ml mobile phase.

HPLC Analysis

Column: Hypersil ODS (250×4.6 mm)

Mobile phase: 40% acetonitrile in water

Flow: 0.8 ml/min

Detection: 220 nm

Inj. Vol.: 50 μl

TABLE 3

Determination of Free LA/DHLA in medium

|  | 1 mg LA/ml medium | | 1.46 mg LAORN/ml medium | |
| --- | --- | --- | --- | --- |
|  | Initial | 60 min | Initial | 60 min |
| LA (mg/ml) | 0.89 | 0.74 | 0.04 | 0.12 |
| DHLA (mg/ml) | 0.08 | 0.27 | bld | bld |
| Sum | 0.97 | 1.01 | 0.04 | 0.12 | bld . . . below limit of detection

TABLE 4

Determination of Total LA/DHLA in medium

|  | 1 mg LA/ml medium | | 1.46 mg LAORN/ml medium | |
| --- | --- | --- | --- | --- |
|  | Initial | 60 min | Initial | 60 min |
| LA (mg/ml) | bld | bld | bld | bld |
| DHLA (mg/ml) | 9.9 | 9.8 | 10.2 | 10.1 |
| Sum | 9.9 | 9.8 | 10.2 | 10.1 | bld . . . below limit of detection

As seen on Table 5, free LA/DHLA was recovered from the cells after 30 and 60 minutes. Not surprisingly, the amounts of free LA/DHLA recovered after incubation with LA was significantly higher than after incubation with LAORN. However, these results provide evidence for a "slow release" of LA from LAORN as Free LA/DHLA could be identified in the medium.

TABLE 5

Determination of Free LA/DHLA in cells

|  | 30 min | 60 min | 30 min | 60 min |
| --- | --- | --- | --- | --- |
| LA (mg/ml) | 0.49 | 0.54 | 0.24 | 0.31 |
| DHLA (mg/ml) | 0.14 | 0.33 | 0.04 | 0.03 |
| Sum | 0.63 | 0.87 | 0.28 | 0.34 |

Table 6 provides results for Total LA/DHLA recovery after incubation with LA or LAORN are presented. As seen, the amount of total LA was found to be significantly higher after LAORN incubation when compared to incubation with LA. These findings support the concept of absorption of LAORN in an oligomeric state.

TABLE 6

Determination of Total LA/DHLA in cells

|  | 30 min | 60 min | 30 min | 60 min |
| --- | --- | --- | --- | --- |
| LA (mg/ml) | bld | bld | bld | bld |
| DHLA (mg/ml) | 0.69 | 0.92 | 1.48 | 1.75 |
| Sum | 0.69 | 0.92 | 1.48 | 1.75 |

These results obtained provide evidence that LAORN is absorbed in oligomeric form. From the comparison between Free and Total LA/DHLA in the cells incubated with LAORN it could be derived that about 80% of the Total LA/DHLA found in the cells were absorbed in oligomeric form.

Under the test conditions chosen it was demonstrated that after incubation with LA for 60 minutes 9.39% were recovered in the cells whereas under the same conditions 17.3% were recovered after incubation with LAORN. Considering that LA was presented in solution to the cells it can be determined that in in-vivo conditions where LA—in steep contrast to LAORN—is much less soluble the difference in absorption might be even higher and more in favor of LAORN.

Results:

The amount of LA and DHLA present in the samples (referred to as "Free LA/DHLA") was compared to the amount observed in the same sample after reduction of LA and LAORN to DHLA (referred to as "Total LA/DHLA").

As seen on Table 5, incubation of LA and LAORN in medium yielded different amounts of Free LA/DHLA. These findings support that LAORN retains its oligomeric structure during the test assay conditions.

As seen on Table 4, both LA and LAORN could be recovered almost completely after reduction to DHLA; hence LA and LAORN are considered stable under the test assay conditions.

Oligomerization Degree of Lipoic Acid Coating Materials

| Lipoic Acid (LA) | Sigma |
| --- | --- |
| Sodium Sulfate | Sigma |
| Absolute Ethanol | Sigma |

Experimental 3.0 g lipoic acid (14.5 mmol) were dissolved in 100 g absolute ethanol with 5 g sodium sulfate. The mixture was stirred for 10 minutes and filtered. The wet weight of the residue was determined. The residue was vacuum dried and the dry weight of the residue determined.

The content of lipoic acid in the dry sodium sulfate was determined to contain about 3.5% lipoic acid (w/w).

The lipoic acid/sodium sulfate residue was subjected, for example, to a temperature at 50° C. for 1 hour to dry the coated sodium sulfate. The average degree of polymerization was determined by the iodine titration method. The table below provides oligomerization and drying times and temperatures.

Results

| Average Polymerization Degree | Content of LA/% | Drying Method |
| --- | --- | --- |
| 2.21* | 3.2 | Room Temperature |
| 3.57 | 3.4 | 50° C. for 0.5 hour |

| Average Polymerization Degree | Content of LA/% | Drying Method |
|---|---|---|
| 3.24 | 3.1 | 50° C. for 1.0 hour |
| 4.15 | 3.5 | 50° C. for 1.5 hour |

*About 80% of lipoic acid is in the free form, not polymer form
LA/% refers to the weight percent of lipoic acid based on the total weight (for example, lipoic acid and sodium sulfate together)

Discussion

It was determined that the lipoic acid on the surface of sodium sulfate oligomerized under minimal elevated temperature. It was noted that an increasing the duration of the heating cycle increased the degree of oligomerization. If the coating was dried at room temperature, the average polymerization was difficult to determine and most of the lipoic acid remained as unoligomerized lipoic acid.

Digestion of Lutein-Esters in Artificial Stomach Acid:

Lutein-esters are naturally occurring derivatives of lutein. Free lutein is susceptible to degradation by light, temperature and/or oxygen. In addition, lutein degrades during the digestion process after oral ingestion. Lutein-esters are deemed to increase the stability of lutein during the digestion process.

To further increase the stability lutein-esters, lutein-esters were coated with lipoic acid as described above with sodium sulfate. The degree of oligomerization for the coating was not determined directly since most iodine would be consumed by the lutein ester. The degree of oligomerization could be indirectly calculated, if desired, (but this was not done) by determining the amount of iodine consumed by lutein ester. This value could then be used to determine the degree of oligomerization of the coating, but the reaction between lutein and iodine is very complex, so it was very difficult to implement in the lab. Therefore, it was assumed that the sodium sulfate "model" provides a reasonable value for the degree of oligomerization of the coating of the coated carotenoid material.

Methods

10±0.5 mg lutein-esters were weighed in a 250 mL round flask and 100 mL artificial stomach or ileal fluid were added. The flask was kept at 37° C. and protected from light while the suspension was stirred continuously. At selected time points (0, 40, 60, 80, 100 minutes), the lutein-esters were extracted into TBME (tert-butylmethylether) (3×30 mL). If applicable, a 5 mL sample was taken for the determination of lipoic acid prior to the extraction with TBME. Lipoic acid was determined after adjustment of the pH to 9.0 (KOH) and incubation at 56° C. for 60 minutes by HPLC.

The combined TBME extracts were filled up to 100 mL with TBME, diluted 1:25 and the extinction was measured by UV/VIS spectroscopy at 450 nm against the solvent (if necessary, the samples were diluted to achieve absorption values below 0.9000). The extinction was corrected by the actual sample weight to yield the absorption/mg sample.

The combined TBME extract was also injected onto a HPLC-system to qualitatively confirm the presence of the lutein-esters and to follow the putative increase of lutein in case of ester hydrolysis.

Lutein-Ester Samples
1) Lutein-ester uncoated
2) Lutein-ester coated with 1% lipoic acid
3) Lutein-ester coated with 3% lipoic acid

| Composition of artificial digestion fluids | | | |
|---|---|---|---|
| Artifical stomach Fluid (100 mL) | | Artificial ileal Fluid (100 mL) | |
| NaCl | 290 mg | KCl | 30 mg |
| KCl | 70 mg | $CaCl_2$ | 50 mg |
| $KH_2PO_4$ | 27 mg | $MgCl_2$ | 20 mg |
| Pepsin | 100 mg | $NaHCO_3$ | 100 mg |
| Mucin | 300 mg | Trypsin | 30 mg |
| HCl | adjustment to pH = 2.0 | Pancreatin | 900 mg |
| | | Bile, lyophilised | 900 mg |
| | | Urea | 30 mg |

HPLC
Pump: isocratic HPLC-pump
Column: YMC C-30 250×4.6 mm
Mobile Phase: TBME/MeOH=50/50 (v/)
Flow Rate: 1 mL/min
Temp.: 30° C.
Detection: 450 nm (UV/VIS detector)

Results

Figure 13:
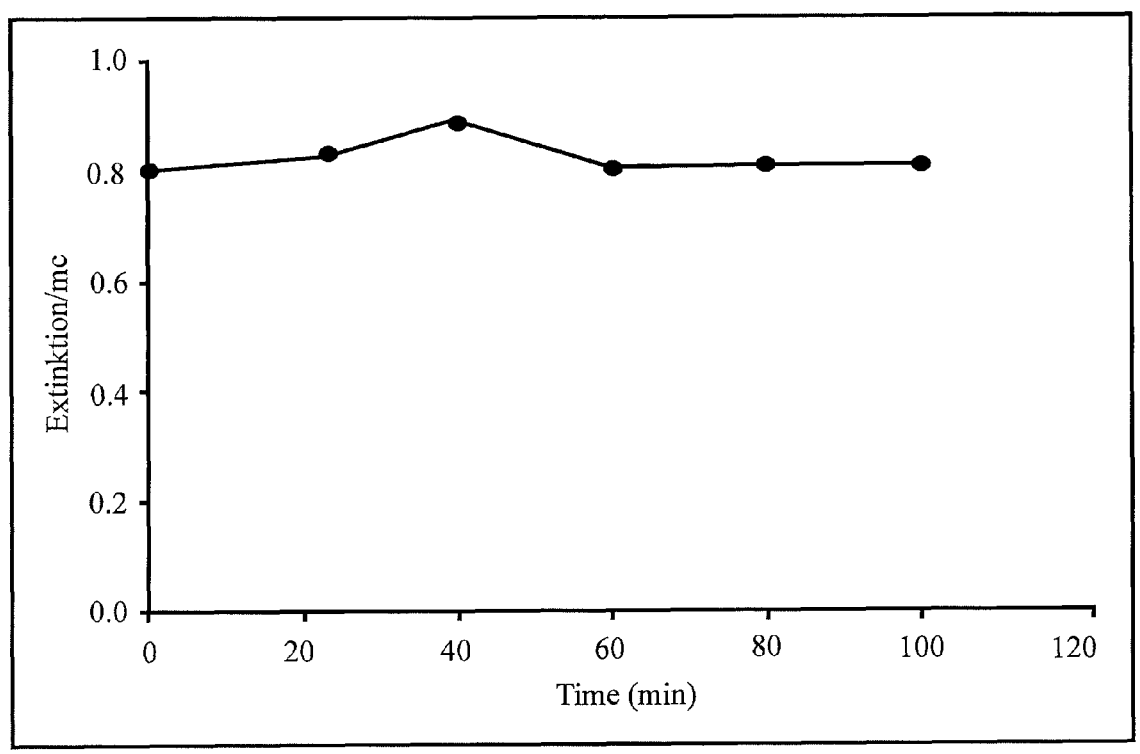
FIG. 13 provides the stability of uncoated lutein-ester in artificial stomach fluid.
Figure 14:
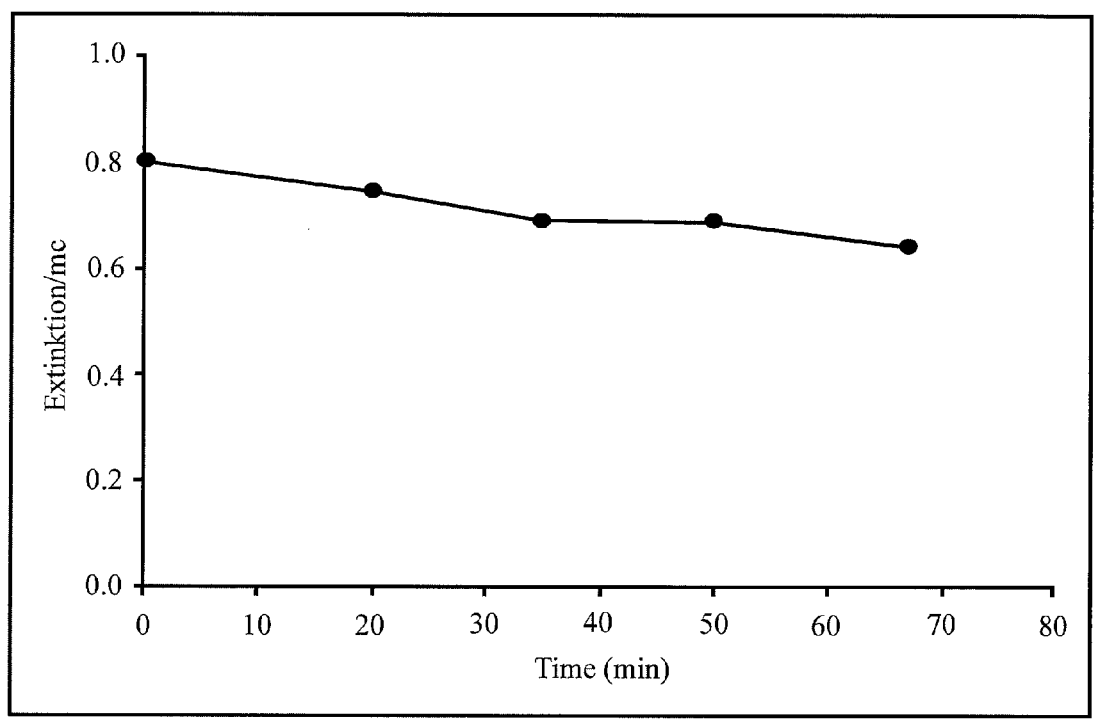
FIG. 14 provides the stability of uncoated lutein-ester in artificial ileal fluid.

The stability of uncoated lutein-ester in artificial stomach or ileal fluid is shown on FIGS. 13 and 14. As seen, uncoated lutein-ester was found to be stable during the stomach digestion, whereas a decay of 20% was observed within 100 minutes of ileal digestion.

Figure 15:
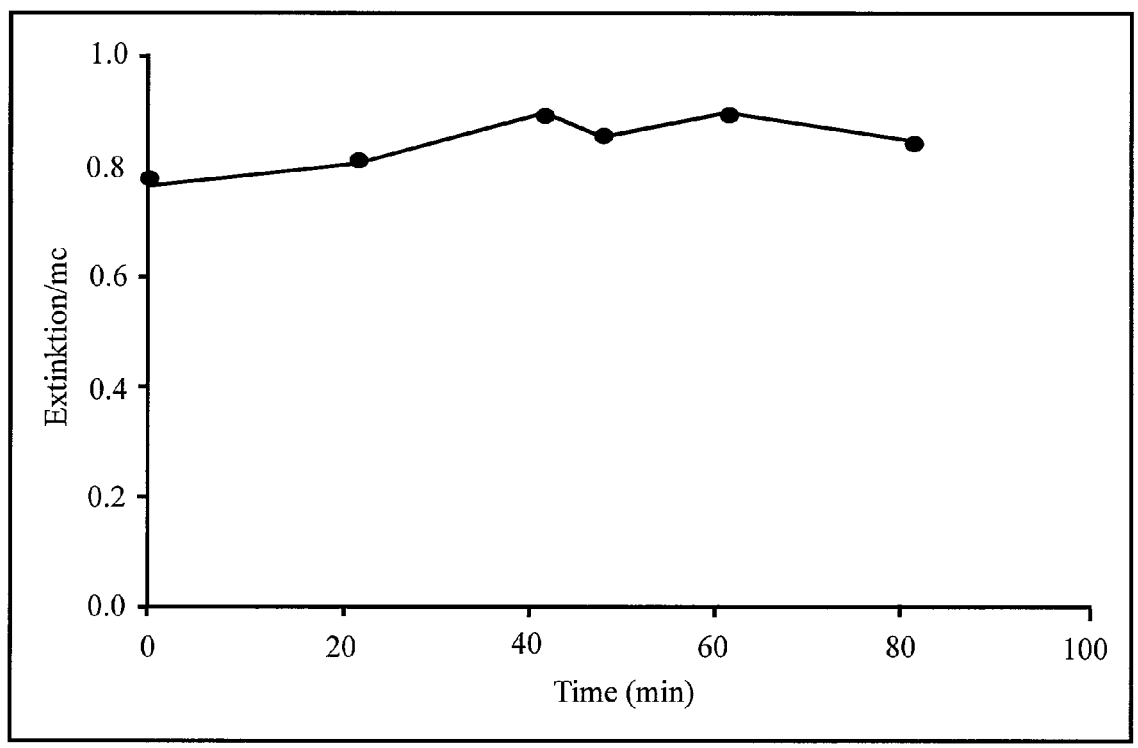
FIG. 15 provides the stability of lutein-esters (1% oligomerized coated lipoic acid) in artificial stomach fluid.
Figure 16:
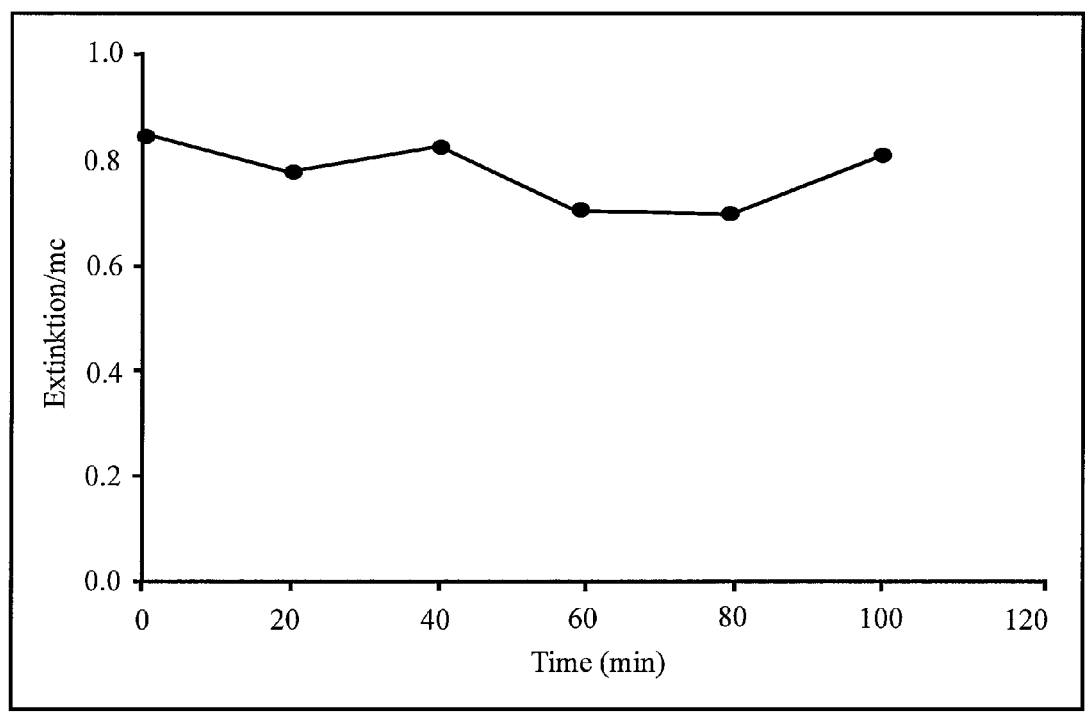
FIG. 16 provides the stability of uncoated lutein-esters (non-oligomerized 1% lipoic acid) in artificial ileal fluid.
Figure 17:
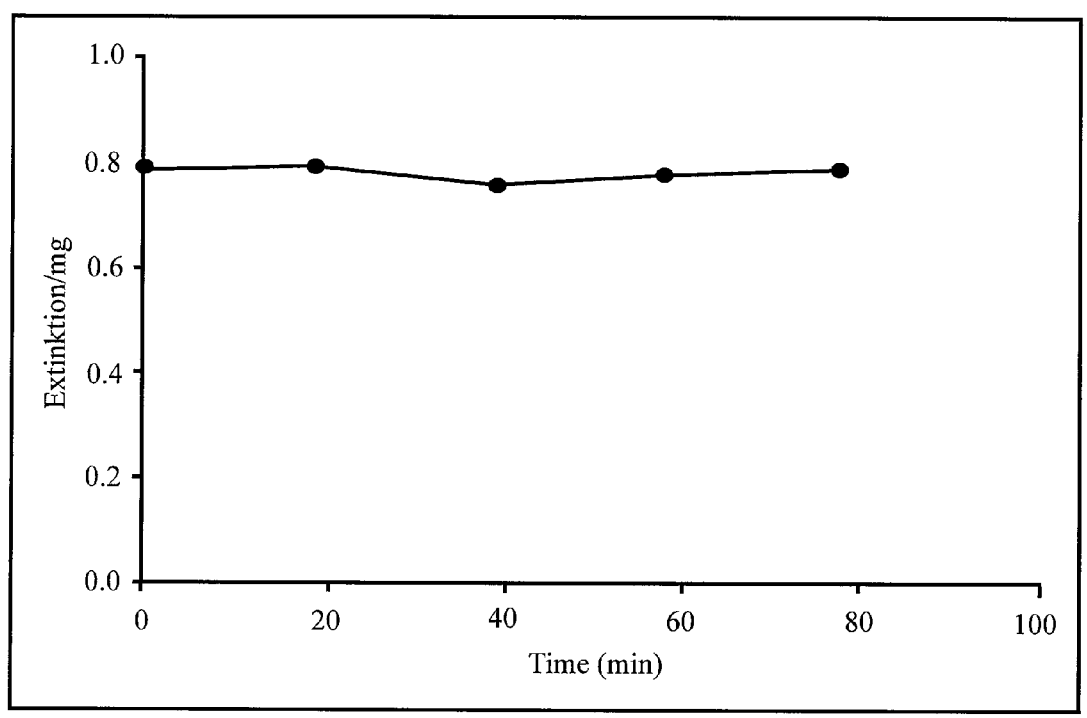
FIG. 17 provides the stability of uncoated lutein-esters (3% oligomerized coated lipoic acid) in artificial stomach fluid.
Figure 18:
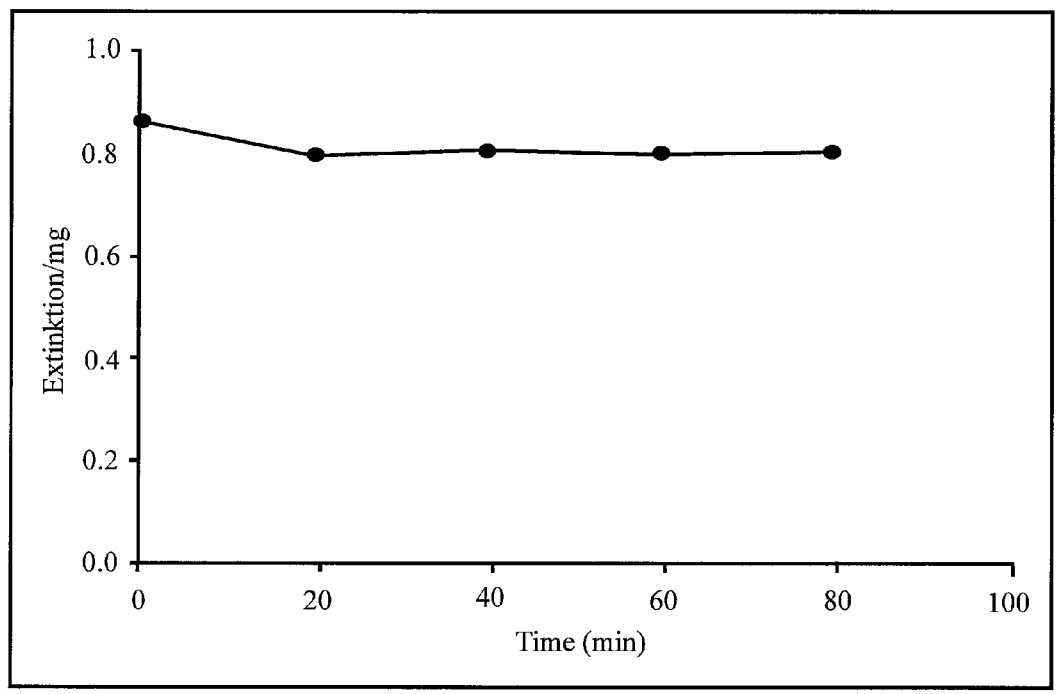
FIG. 18 provides the stability of uncoated lutein-esters (non-oligomerized 3% lipoic acid) in artificial ileal fluid.
Figure 19:
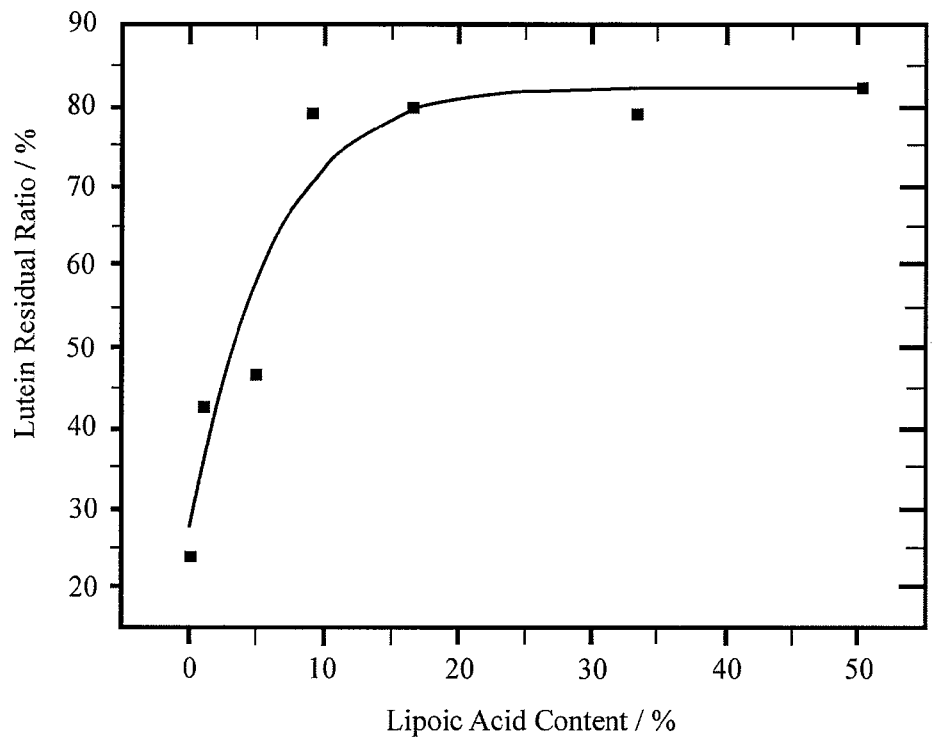
FIG. 19 depicts a curve for lipoic acid content and residual ratio of lutein esters.

The stability of lutein-esters coated with 1% oligomerized lipoic acid in artificial stomach or ileal fluid is shown on FIGS. 15 and 16 (non-oligomerized). As seen, lutein-esters coated with 1% lipoic acid were found to be stable during the stomach and the ileal digestion.

Conclusion:

Uncoated lutein-ester was found to be stable at pH=2.0 (artificial stomach fluid), hence coating does not exert an effect during stomach acid digestion. On the other hand, coating with 1 or 3% lipoic acid prevents degradation during the artificial ileal digestion. No concentration dependent effect was seen.

Based on the preliminary determination of lipoic acid, the coating is stable at pH=2.0 and is degraded at pH=7.5.

Comparison of Lipoic Acid and Citric Acid in the Protection of Lutein

Experimental 1.0 g citric acid was added to 100 g absolute ethanol with 5 g lutein esters. The mixture was stirred for 10 minutes and filtered. The wet weight of the residue was determined. The residue was vacuum dried and the dry weight of the residue determined. The content of citric acid in the lutein esters was determined to contain about 1% citric acid (w/w).

The dried citric acid lutein ester mixture was subjected to an elevated temperature of 50° C. for 24 hours. The lutein content was measured by the UV-Visible spectrophotometric method as described above.

Oligomerized lipoic acid coated lutein esters were prepared and dried as described above for citric acid but with substitution of citric acid with lipoic acid.

Results

| Sample name | Residual Ratio/% |
|---|---|
| Blank Sample | 8.8 |
| 1% Citric Acid Coated Sample | 90.9 |
| 5% Citric Acid Coated Sample | 95.9 |
| 1.5% Lipoic acid Coated Sample | 97.8 |

"Blank sample" is lutein ester subjected to an elevated temperature of 50° C. for 24 hours.
"Residual ratio/% refers to the content of lutein after the experiment and the content of lutein before the experiment.

Conclusions

The citric acid coated lutein esters were found to be stabilized relative to an untreated sample lutein sample (blank sample The protective effect of citric acid was less than oligomerized lipoic acid coating especially in view of a weight basis.

Comparison of Lipoic Acid and Polyphenols in the Protection of Lutein Esters

Experimental 1.0 g gallic acid was dissolved in 100 g absolute ethanol with 5 g lutein esters. The mixture was stirred for 10 minutes and filtered. The wet weight of the residue was determined. The residue was vacuum dried and the dry weight of the residue determined.

The content of gallic acid in the lutein esters was determined to contain about 1% gallic acid (w/w).

The gallic acid/lutein ester mixture was then subjected to an elevated temperature at 60° C. for 9 hours. The lutein content was measured with the UV-Visible spectrophotometric method as described above.

Oligomerized lipoic acid coated lutein esters were prepared and dried as described above for gallic acid but with substitution of gallic acid with lipoic acid.

Results

| Sample name | Residual Ratio/% |
| --- | --- |
| Blank Sample | — |
| 1% Gallic Acid Coated Sample* | 60.9 |
| 2% Resveratrol Sample** | 62.1 |
| 3.5% Lipoic acid Coated Sample | 95.8 |

*a representative polyphenol
**polyphenols extract from berry and grape leaf
"Blank sample" is lutein ester subjected to an elevated temperature of 60° C. for 9 hours.
"Residual ratio/% refers to the content of lutein after the experiment and the content of lutein before the experiment.

Conclusions

The oligomerized lipoic acid coated lutein esters are stable and the polyphenols also have a protective effect on lutein esters.

Comparison of Lipoic Acid and Vitamin E in the Protection of Lutein Esters

Experimental 300 mg lutein esters and 30 mg α-Tocopherol were added to a mortar, completely milled and maintained at a temperature of 60° C. for 4 hours. The lutein content was measured with the UV-Visible spectrophotometric method as described above.

A sample of coated lutein esters with 1% lipoic acid (based on the weight of ester) was prepared by completely milling the two materials followed by treatment at an elevated temperature of 60° C. for 4 hours to afford oligomerized lipoic acid containing lutein esters and to simulate accelerated degradation of the ester. The lutein content was measured with a UV-Visible spectrophotometer as described above.

Results

| Sample name | Residual Ratio/% |
| --- | --- |
| Blank sample | 24.1 |
| 1% α-Tocopherol sample | 24.8 |
| 10% α-Tocopherol sample | 77.9 |
| 1% Lipoic acid Coated Sample | 93.8 |
| 4.7% Lipoic acid Coated Sample | 94.5 |

"Blank sample" is lutein ester subjected to an elevated temperature of 60° C. for 4 hours.
"Residual ratio/% refers to the content of lutein after the experiment and the content of lutein before the experiment.

Conclusion

Both oligomerized lipoic acid and α-tocopherol protected the lutein ester from degradation however, the amount of lipoic acid oligomer required was much less than the amount of α-Tocopherol required.

Methods to Stabilize Lutein Esters

Materials

| | |
| --- | --- |
| Lutein esters | Extract from Marigold Olesin |
| Lipoic Acid | Sigma |
| Gallic Acid | Sigma |
| Resveratrol | Sigma |
| Absolute Ethanol | Sigma |

Experimentals

Mixing Method 300 mg lutein esters and a predetermined amount of lipoic acid were placed in a mortar, milled and then subjected to an elevated temperature of 60° C. for 4 hours. The lutein content was determined by the UV-Visible spectrophotometric method described above.

Coating Method 3.0 g lipoic acid (14.5 mmol) were dissolved in 100 g absolute with 5 g lutein esters. The mixtures was stirred for 10 minutes and filtered. The wet weight of the residue was determined. The residue was vacuum dried and the dry weight of the residue determined. The content of lipoic acid in the lutein esters was determined to contain about 3.5% lipoic acid (w/w).

The mixture of lipoic acid/lutein esters was then subjected to an elevated temperature of 60° C. for 9 hours to effect oligomerization of the lipoic acid. The lutein content was determined by the UV-Visible spectrophotometric method described above.

Results

Mix Method

| Residual Ratio after Durability Experiment | | |
| --- | --- | --- |
| Dosage of LA/mg | Content of LA/% | Residual Ratio/% |
| 0 | 0.0 | 24.1 |
| 3 | 1.0 | 42.7 |
| 15 | 4.8 | 46.5 |
| 30 | 9.1 | 79.5 |
| 60 | 16.7 | 80.1 |
| 150 | 33.3 | 79.4 |
| 300 | 50.0 | 82.4 |

"Residual ratio/% refers to the content of lutein after the experiment and the content of lutein before the experiment as determined by UV-VIS spectroscopy.

Coating Method

| Residual Ratios after Durability Experiment | |
| --- | --- |
| Sample name | Residual Ratio/% |
| Blank Sample | — |
| 1% Gallic Acid Coated Sample | 60.9 |
| 2% Resveratrol Coated Sample | 62.1 |
| 3.5% Lipoic acid Coated Sample | 95.8 |

"Residual ratio/% refers to the content of lutein after the experiment and the content of lutein before the experiment.

The gallic acid and resveratrol coated samples were prepared similarly to the lipoic acid coated samples described above by substituting either gallic acid or resveratrol for lipoic acid.

Conclusions

It was noted that oligomerized lipoic acid protected the lutein ester and that with the increase of dosage, the stability of the lutein ester was also increased. For mixing the components together, an ideal dosage of lipoic acid was about 10% (based on the total weight of lutein ester. It was also determined that by the coating method, both polyphenol and oligomerized lipoic acid could protect lutein esters from degradation; however, that the oligomerized lipoic acid being much more efficient for the prevention of degradation. It was further noted that the coating method was more efficient than simply mixing the components intimately together. It was notable that with equivalent amounts of lipoic acid or other stabilizer utilized and longer heating times for the mixed components, the coating method sample has a larger residual ratio than by mixing of the components together.

Polymerization Degree of Lipoic Acid Derivatives as Coating Material

Coating Method 3.0 g LAORN (8.42 mmol) were dissolved in 100 g water with 5 g silica gel. The mixture was stirred for 10 minutes and filtered. The wet weight of the material was determined and was then vacuum dried. The dry weight of the material was then determined.

The amount of LAORN coated onto silica gel was determined and found to be about 2.6% LAORN (w/w).

The average degree of polymerization was determined by the iodine titration method described above. Other samples of oligo-lipoic acid salts were prepared as described for LAORN.

Determination of Degree of Polymerization

The average degree of polymerization of the various oligo-lipoic acid salts were determined by the iodometric method described above.

Results

| Dry at room temperature | | |
|---|---|---|
| Sample Name | Polymerization degree before coating | Polymerization degree after coating |
| LAORN | 4.21 | 5.14 |
| NH$_3$ lipoic acid | 10.86 | 11.65 |
| Na lipoic acid | 14.17 | 14.56 |

| Dry at 5° C. | | |
|---|---|---|
| Sample Name | Polymerization degree before coating | Polymerization degree after coating |
| LAORN | 4.21 | 4.35 |
| NH$_3$ lipoic acid | 10.86 | 11.22 |
| Na lipoic acid | 14.17 | 14.01 |

"Dry at 5° C." means that the sample was dried at 5° C. under vacuum "room temperature" samples were dried at room temperature under vacuum.

Conclusions

The degree of polymerization for the various oligo-alpha lipoic acid salts are stable before and after the coating process.

Stability Test

Preparation:

3.0 g LAORN (8.42 mmol) were dissolved in 100 g water with 5 g lutein ester. The mixture was stirred for 10 minutes and filtered. The wet weight of the solids were measured. The solids were then vacuum dried and the residue was measured when dried.

The average degree of polymerization was determined by the iodine titration method described above. Additional samples of oligo-lipoic acid salts were made similarly to that of LAORN.

Test:

Samples were subjected to a temperature at 50° C. for 24 hours. The lutein content was then measured by UV-Visible spectrophotometry.

Experiment Results:

| Sample Name | Temperature of Dry | Residual Ratio/% |
|---|---|---|
| LAORN | Dry at room temperature | 95.8 |
| NH$_3$ lipoic acid | | 97.8 |
| Na lipoic acid | | 95.2 |
| LAORN | Dry at 5° C. | 97.2 |
| NH$_3$ lipoic acid | | 92.6 |
| Na lipoic acid | | 91.2 |

Conclusions:

The above coated lutein esters were found to be stable in the aging test. The protective effect was similar amongst the various oligomeric lipoic acid complexes test and it was noted that drying temperatures of the mixtures did not effect the ability of the complexes to protect the lutein esters.

Preparation of Arg-La Salt:

To 17.4 g (0.1 mol) Arginine base and 720 ml water was added 20.6 g (0.1 mol) lipoic acid with stirring. The lipoic acid slowly dissolved to form a clear yellow liquid. The liquid was then spray dried to afford about 40 g Arg-LA salt with a degree of polymerization of about 2.55 to 2.91.

Although the present invention has been described with reference to preferred embodiments, persons skilled in the art will recognize that changes may be made in form and detail without departing from the spirit and scope of the invention. All references cited throughout the specification, including those in the background, are incorporated herein in their entirety. Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A composition comprising:
   a stable complex of oligomeric lipoic acid and a counterion, wherein the average degree of oligomerization is between 2 and about 7 and has a melting point above that of monomeric lipoic acid and the counterion is a basic amino acid.

2. The composition of claim 1, wherein the basic amino acid is ornithine, arginine, lysine or mixtures thereof.

3. A composition comprising:
   a stable oligomeric lipoic acid complex and a counterion comprising formula (I):

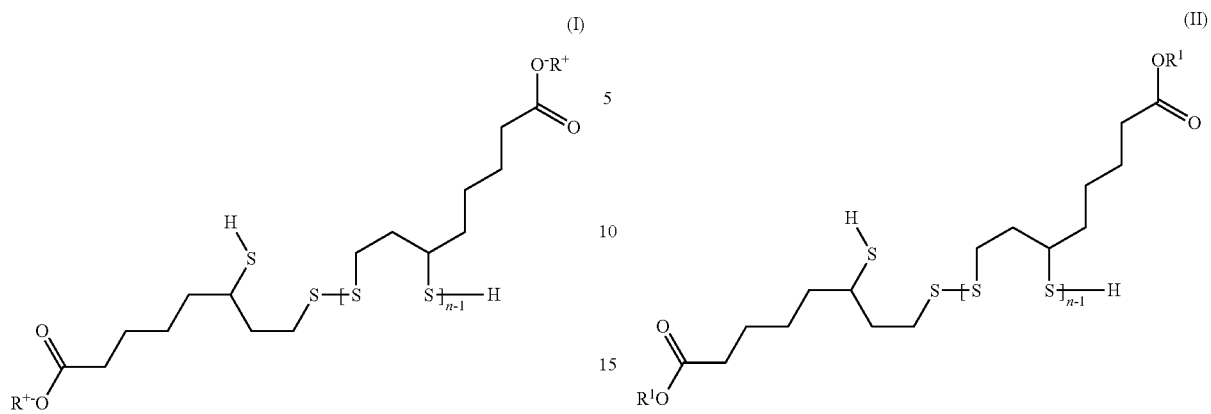

wherein each $R^+$ independently denote a counterion, and n is a value between about 2 and about 50 and has a melting point above that of monomeric lipoic acid and the counterion is a basic amino acid.

4. The composition of claim 3 wherein the basic amino acid is ornithine, arginine, lysine or mixtures thereof.

5. A stable oligomeric lipoic acid complex and a basic amino acid counterion prepared by the process of:

a) reacting a basic amino acid with lipoic acid in an aqueous solution;

b) maintaining the solution at an elevated temperature for a period of between about 1 to about 5 hours; and c) precipitating a complex of the oligomeric lipoic acid and basic amino acid counterion from the aqueous solution by addition of a non-solvent wherein the degree of oligomerization is between 2 and about 50 and has a melting point above that of monomeric lipoic acid.

6. The oligomeric lipoic acid complex of the process of claim 5, further comprising the step of:

d) collecting the precipitated complex.

7. The oligomeric lipoic acid complex of claim 5, wherein the temperature of the reaction is between about 30° C. and about 50° C.

8. The oligomeric lipoic acid complex of claim 5, wherein the solution was maintained at the elevated temperature for about 3 hours.

9. The oligomeric lipoic acid complex of claim 5, wherein the non-solvent is an alcohol, a chlorinated hydrocarbon, an aliphatic ketone, an aliphatic ether, an alkyl hydrocarbon, an aromatic hydrocarbon or mixtures thereof.

10. The oligomeric lipoic acid complex of claim 9, wherein the non-solvent is one of acetonitrile, dichloromethane, acetone, 2-propanol, diethyl ether, hexane, octane, toluene, petroleum ether, tetrahydrofuran, octanol, benzene, dioxane or mixtures thereof.

11. The oligomeric lipoic acid complex of claim 5, wherein the amino acid is ornithine, arginine, lysine or mixtures thereof.

12. A composition comprising:

a stable mixed oligomeric alpha lipoic acid complex and a counterion comprising formula (II):

wherein n is a value between about 2 and about 7 and has a melting point above that of monomeric lipoic acid; and each $R^1$ independently is a hydrogen atom or counterion provided at least one $R^1$ is a counterion and the counterion is a basic amino acid.

13. A pharmaceutical composition comprising the composition of claim 1 and a pharmaceutically acceptable carrier.

14. A pharmaceutical composition comprising the composition of claim 3 and a pharmaceutically acceptable carrier.

15. A pharmaceutical composition comprising the composition of claim 5 and a pharmaceutically acceptable carrier.

16. A pharmaceutical composition comprising the composition of claim 12 and a pharmaceutically acceptable carrier.

17. A composition comprising:

an isolated complex of oligomeric lipoic acid and a counterion, wherein the degree of oligomerization is between 2 and about 7 and has a melting point above that of monomeric lipoic acid and the counterion is a basic amino acid.

18. The composition of claim 17, wherein the basic amino acid is ornithine, arginine, lysine or mixtures thereof.

19. A composition comprising:

an isolated oligomeric lipoic acid complex and a counterion comprising formula (I):

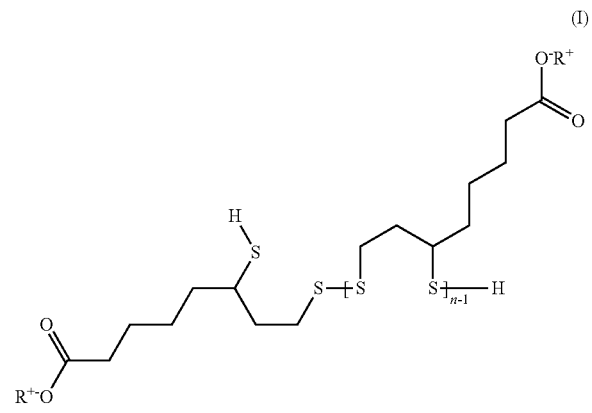

wherein each $R^+$ independently denote a counterion, and n is a value between about 2 and about 7 and has a melting point above that of monomeric lipoic acid and the counterion is a basic amino acid.

20. The composition of claim 19, wherein the basic amino acid is ornithine, arginine, lysine or mixtures thereof.

21. A composition comprising:

an isolated mixed oligomeric alpha lipoic acid complex and a counterion comprising formula (II):

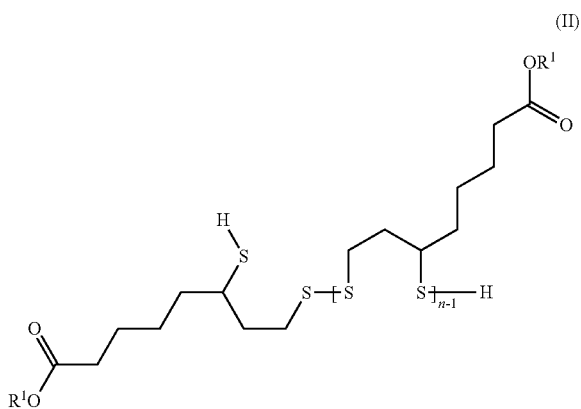

wherein n is a value between about 2 and about 7 and has a melting point above that of monomeric lipoic acid; and each $R^1$ independently is a hydrogen atom or counterion provided at least one $R^1$ is a counterion and the counterion is a basic amino acid.

22. A pharmaceutical composition comprising the composition of claim 17 and a pharmaceutically acceptable carrier.

23. A pharmaceutical composition comprising the composition of claim 19 and a pharmaceutically acceptable carrier.

24. A pharmaceutical composition comprising the composition of claim 21 and a pharmaceutically acceptable carrier.

25. The composition of claim 1, wherein the complex has a melting point up to between about 165° C. and 170° C.

26. The composition of claim 3, wherein the complex has a melting point between about 165° C. and 170° C.

27. The composition of claim 5, wherein the complex has a melting point between about 165° C. and 170° C.

28. The composition of claim 12, wherein the complex has a melting point between about 165° C. and 170° C.

29. The composition of claim 17, wherein the complex has a melting point between about 165° C. and 170° C.

30. The composition of claim 19, wherein the complex has a melting point between about 165° C. and 170° C.

31. The composition of claim 21, wherein the complex has a melting point between about 165° C. and 170° C.

* * * * *